US009200320B2

(12) United States Patent
Korlach et al.

(10) Patent No.: US 9,200,320 B2
(45) Date of Patent: Dec. 1, 2015

(54) REAL-TIME SEQUENCING METHODS AND SYSTEMS

(71) Applicant: Pacific Biosciences of California, Inc., Menlo Park, CA (US)

(72) Inventors: Jonas Korlach, Newark, CA (US); Stephen Turner, Menlo Park, CA (US); Eric Schadt, Rye, NY (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 14/571,892

(22) Filed: Dec. 16, 2014

(65) Prior Publication Data

US 2015/0105273 A1 Apr. 16, 2015

Related U.S. Application Data

(63) Continuation of application No. 13/924,130, filed on Jun. 21, 2013, now Pat. No. 8,940,507, which is a continuation of application No. 12/767,673, filed on Apr. 26, 2010, now Pat. No. 8,501,405.

(60) Provisional application No. 61/186,661, filed on Jun. 12, 2009, provisional application No. 61/173,060, filed on Apr. 27, 2009.

(51) Int. Cl.
*C12Q 1/68* (2006.01)
*C12Q 1/70* (2006.01)

(52) U.S. Cl.
CPC .............. *C12Q 1/6869* (2013.01); *C12Q 1/702* (2013.01)

(58) Field of Classification Search
None
See application file for complete search history.

(56) References Cited

U.S. PATENT DOCUMENTS

| | | | |
|---|---|---|---|
| 5,547,839 A | 8/1996 | Dower et al. | |
| 5,648,245 A | 7/1997 | Fire et al. | |
| 5,714,320 A | 2/1998 | Kool | |
| 5,723,584 A | 3/1998 | Schatz | |
| 5,874,239 A | 2/1999 | Schatz | |
| 5,932,433 A | 8/1999 | Schatz | |
| 6,210,896 B1 | 4/2001 | Chan | |
| 6,255,083 B1 | 7/2001 | Williams | |
| 6,265,552 B1 | 7/2001 | Schatz | |
| 6,787,308 B2 | 9/2004 | Balasubramanian et al. | |
| 6,917,726 B2 | 7/2005 | Levene et al. | |
| 7,052,847 B2 | 5/2006 | Korlach et al. | |
| 7,056,661 B2 | 6/2006 | Korlach et al. | |
| 7,170,050 B2 | 1/2007 | Turner et al. | |
| 7,270,951 B1 | 9/2007 | Stemple et al. | |
| 7,476,503 B2 | 1/2009 | Turner et al. | |
| 7,727,722 B2 | 6/2010 | Nelson et al. | |
| 2002/0102586 A1 | 8/2002 | Ju et al. | |
| 2003/0064366 A1 | 4/2003 | Hardin et al. | |
| 2003/0096253 A1 | 5/2003 | Nelson et al. | |
| 2003/0190647 A1 | 10/2003 | Odera | |
| 2003/0215862 A1 | 11/2003 | Parce et al. | |
| 2004/0048300 A1 | 3/2004 | Sood et al. | |
| 2004/0152119 A1 | 8/2004 | Sood et al. | |
| 2004/0224319 A1 | 11/2004 | Sood et al. | |
| 2006/0061754 A1 | 3/2006 | Turner et al. | |
| 2006/0166203 A1 | 7/2006 | Tooke | |
| 2007/0231810 A1 | 10/2007 | Todd et al. | |
| 2007/0275387 A1 | 11/2007 | Ju | |
| 2008/0299565 A1 | 12/2008 | Schneider et al. | |
| 2009/0208961 A1 | 8/2009 | Bjornson et al. | |
| 2010/0190151 A1 | 7/2010 | Quake et al. | |

FOREIGN PATENT DOCUMENTS

| | | |
|---|---|---|
| WO | WO 91/06678 A1 | 5/1991 |
| WO | WO 96/27025 A1 | 9/1996 |
| WO | WO 99/05315 A2 | 2/1999 |
| WO | WO 2004/074503 A2 | 9/2004 |
| WO | WO 2006/125012 A2 | 11/2006 |
| WO | WO 2009/037473 A2 | 3/2009 |
| WO | WO 2009/124255 A2 | 10/2009 |

OTHER PUBLICATIONS

Beckett, D., et al., Protein Sci 8:921-9 (1999).
Bibillo, a., et al., J. Biol Chem 277: 34836-45 (2002).
Bowman, et al., J. Virology 72(6):5198-5206 (1998).
Eid, et al., Science 323:133-138 (2009).
Foquet, M., et al., J. Appl. Phys. 103:034301-9(2008).
Giraut, et al., ChemBioChem 10:2246-2252 (2009).
Gregerson, D. S., et al., Biochemistry 19:301-6 (1980).
Korlach, J., et al. Nucleos. Nucleic Acids 27:1072-1083 (2008).
Korlach, J., et al., Proc Natl Acad Sci USA 105:1176-1181 (2008).
Kumar, et al., Nucleos. Nucleot. Nucleic Acids 24(5-7):401-408 (2005).
Lagunavicius, et al., RNA 15:765-771 (2009).
Levene, et al., Science 299 (5607):682-686 (2003).
Limbach, et al., Nuc. Ac. Res. 22(12):2183-2196 (1994).
Lipson, et al., <<Quantification of the Yeast Transcriptome by Single-Molecule Sequencing,>> Nature Biotech. (2009) 27(7): 652-658.
Liu, et al., FEBS Letters 580(5):1497-1501 (2006).
Lundquist, P. M., et al., Optics Letters 33:1026-8 (2008).
Mader, et al., J. Lab. Clin. Med. 137(6):422-428 (2001).
Makeyev, E. V., et al., EMBO J 19:124-33 (2000).
Makeyev, et al., RNA 7:774-781 (2001).
Moore, et al., Science 256:992-997 (1992).
Mulder, et al., Nuc. Ac. Res. 33(15):4865-4873 (2005).

(Continued)

*Primary Examiner* — James Martinell
(74) *Attorney, Agent, or Firm* — Morgan, Lewis & Bockius LLP

(57) ABSTRACT

The present invention is generally directed to compositions, methods, and systems for performing single-molecule, real-time analysis of a variety of different biological reactions. The ability to analyze such reactions provides an opportunity to study those reactions as well as to potentially identify factors and/or approaches for impacting such reactions, e.g., to either enhance or inhibit such reactions. In certain preferred embodiments, RNA templates are used in single-molecule real-time sequencing reactions.

15 Claims, 17 Drawing Sheets

(56) References Cited

OTHER PUBLICATIONS

Myers, et al., Biochemistry 30(31):7661-7666 (1991).
Ozsolak, et al., Nature 461:814-818 (2009) [including online supplement].
Pascal, J. M., Curr. Op. in Struct. Biol. 18:96-105 (2008).
Ricchetti, et al., EMBO J. 12(2):387-396 (1993).
Silber, et al., Proc. Nat. Acad. Sci. USA 69(10):3009-3013 (1972).
Sims, et al. Poster—"Toward Single Cell, Single Molecule, Digital mRNA Pro_ling with No PCR Amplication," Harvard University, Presented at NHGRI Meeting, Mar. 10-11, 2010.
Sood et al., J. Amer. Chem. Soc., 127: 2394 (2005).
Tan, et al., "Functional Characterization of RNA-Dependent DNA Polymerase and RNase H Activities of a Recombinant HIV Reverse Transriptase," Biochemistry 30(10):2651-2655 (1991).
Tang, et al., Nature Methods 6(5):377-382 (2009) [including online supplement].
Zhu, et al., Cytometry 28(3):206-211 (1997).

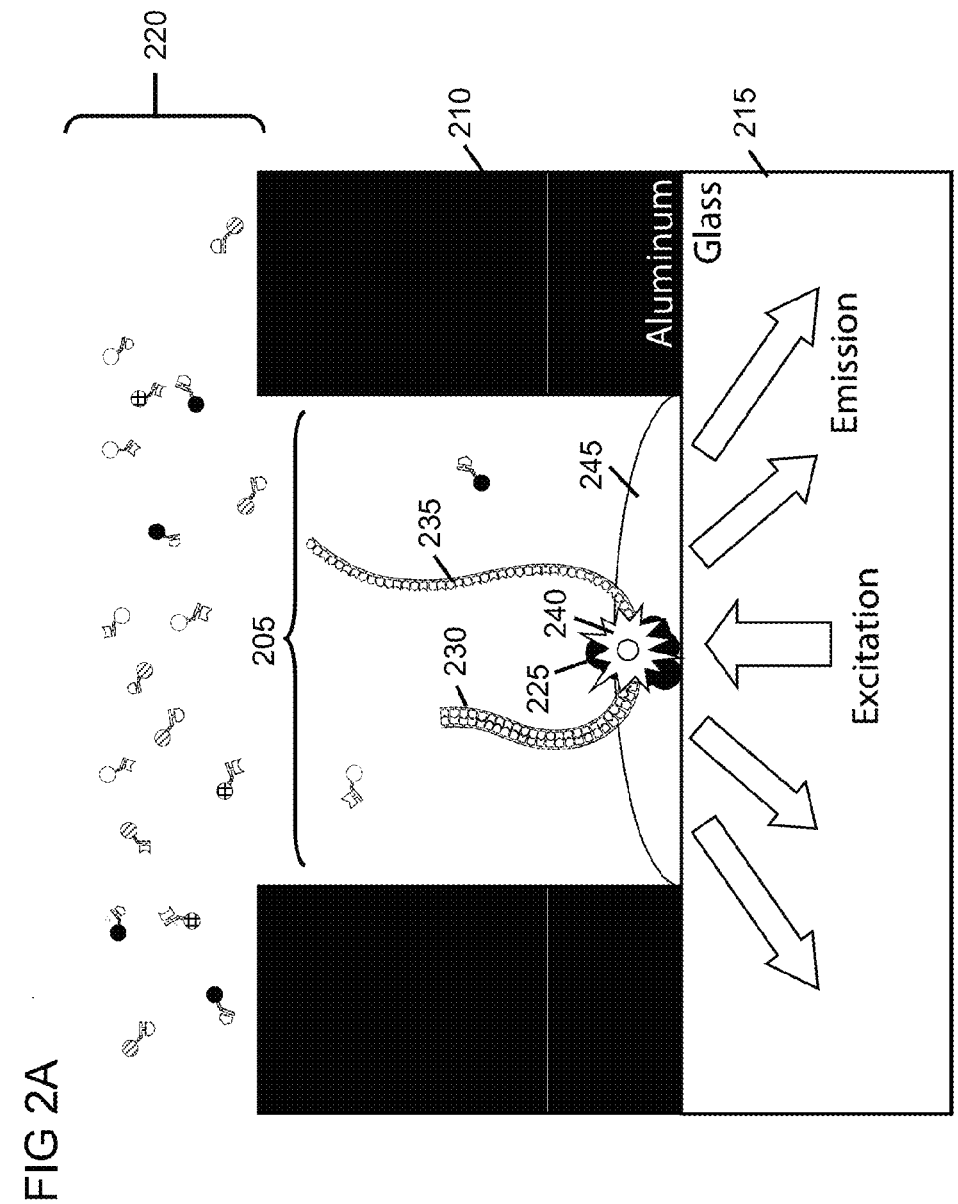

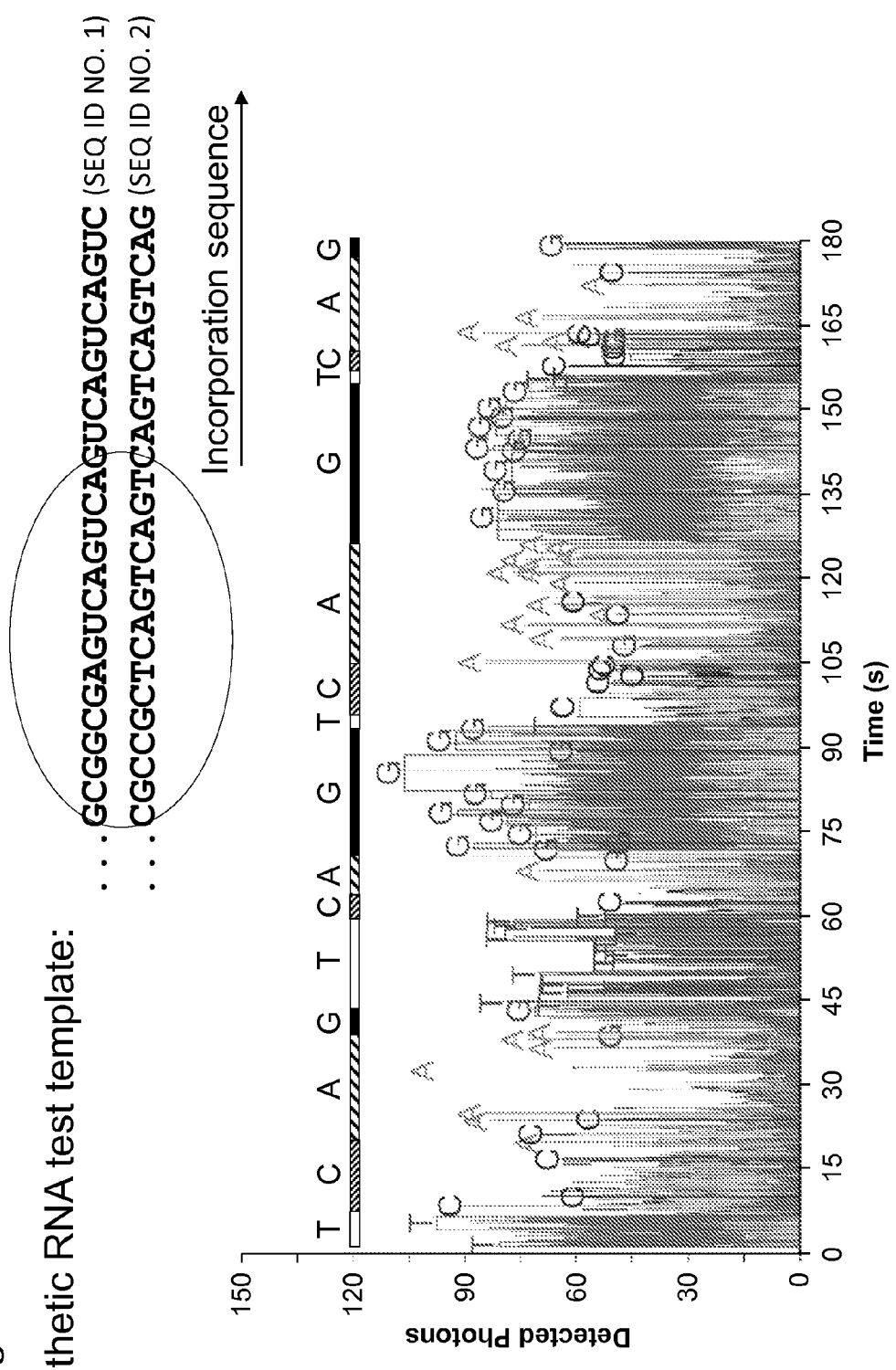

FIG 5C

| | $K_{cat}$ (s$^{-1}$) | $K_m$ (μM) |
|---|---|---|
| dATP | 30 ± 3.0 | 4.9 ± 1.3 |
| Phospholinked dATP | 1.3 ± 0.1 | 3.5 ± 0.1 |
| dCTP | 19 ± 0.8 | 1.5 ± 0.2 |
| Phospholinked dCTP | 1.0 ± 0.1 | 1.9 ± 0.2 |
| dGTP | 18 ± 1.2 | 0.5 ± 0.2 |
| Phospholinked dGTP | 1.1 ± 0.1 | 0.9 ± 0.1 |
| dTTP | 17 ± 0.4 | 2.1 ± 0.2 |
| Phospholinked dTTP | 0.8 ± 0.1 | 0.6 ± 0.1 |

Pseudouridine (Ψ,Y):

N²-methylguanosine (m²G):

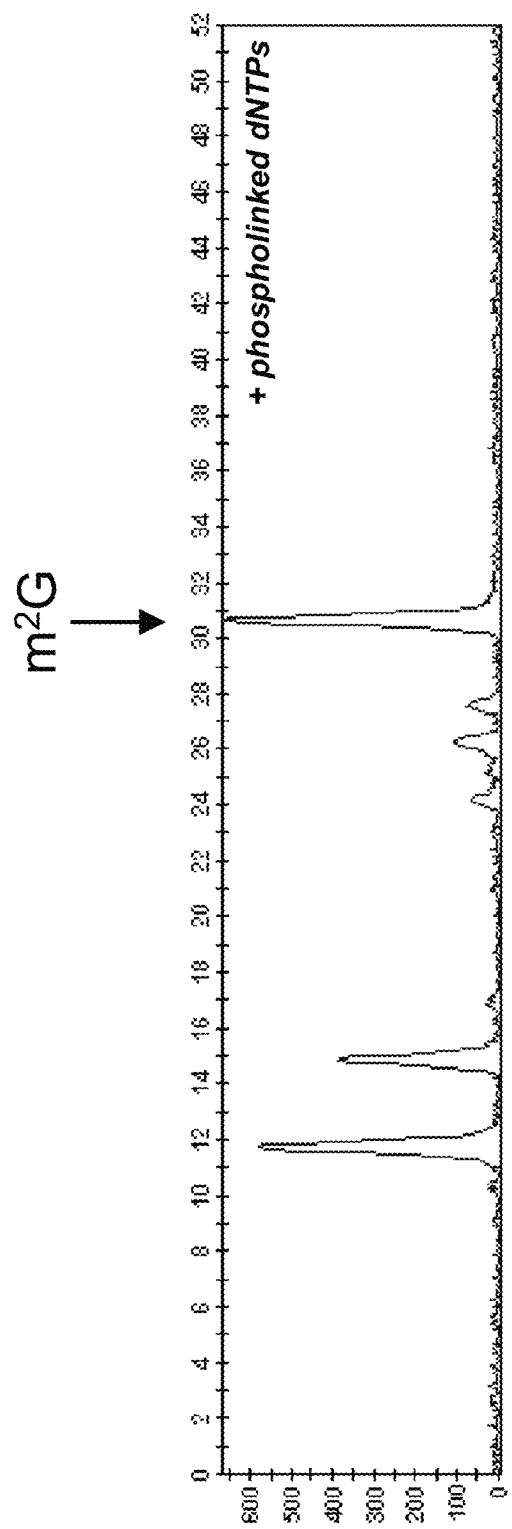
FIG. 7C Bulk comparison:

A. − NTPs
B. + NTPs
C. 3 NTPs + phospholinked NTP 1
D. 3 NTPs + phospholinked NTP 2
E. 3 NTPs + phospholinked NTP 3

REAL-TIME SEQUENCING METHODS AND SYSTEMS

CROSS-REFERENCE TO RELATED APPLICATIONS

This application is a continuation of U.S. Ser. No. 13/924,130, filed Jun. 21, 2013, which a continuation of U.S. Ser. No. 12/767,673, filed Apr. 26, 2010, now U.S. Pat. No. 8,501,405, which claims the benefit of U.S. Ser. No. 61/173,060, filed Apr. 27, 2009, and U.S. Ser. No. 61/186,661, filed Jun. 12, 2009, the disclosures of which are incorporated herein by reference in their entireties for all purposes.

STATEMENT REGARDING FEDERALLY SPONSORED RESEARCH

Not Applicable.

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

A stereotypical example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, a variety of kinase enzymes have been identified as key pathway components in a number of therapeutically relevant biological pathways, as they will often phosphorylate different substrate proteins upon the binding of different effector compounds, e.g., cytokines, to receptors on biological proteins, e.g., cell surface receptors. By modeling the kinase reaction system in vitro, and testing it against libraries of potential pharmaceutical candidates, one can identify the compounds which best inhibit or enhance the reaction in question.

Typically, modeled biological systems rely on bulk reactions that ascertain general trends of biological reactions and provide indications of how such bulk systems react to different effectors. While such systems are useful as models of bulk reactions in vivo, a substantial amount of information is lost in the averaging of these bulk reaction results. In particular, the activity of and effects on individual molecular complexes cannot generally be teased out of such bulk data collection strategies.

Single-molecule real-time analysis of nucleic acid synthesis has been shown to provide powerful advantages over nucleic acid synthesis monitoring that is commonly exploited in sequencing processes. In particular, by concurrently monitoring the synthesis process of nucleic acid polymerases as they work in replicating nucleic acids, one gains advantages of a system that has been perfected over millions of years of evolution. In particular, the natural nucleic acid synthesis processes (e.g., DNA-dependent DNA synthesis, DNA-dependent RNA synthesis, RNA-dependent RNA synthesis and RNA-dependent cDNA synthesis) provide the ability to copy information from genomic DNA or replicate RNA genomes in extremely short periods of time, and do so with an extremely high level of fidelity to the underlying template being replicated.

BRIEF SUMMARY OF THE INVENTION

The present invention is generally directed to compositions, methods, and systems for performing single-molecule, real-time analysis of a variety of different biological reactions. The ability to analyze such reactions provides an opportunity to study those reactions as well as to potentially identify factors and/or approaches for impacting such reactions, e.g., to either enhance or inhibit such reactions. In certain embodiments, analytical reactions are performed that provide sequence information or "reads" for a single nucleic acid template, preferably a template comprising RNA.

In certain aspects, methods are provided for sequencing an mRNA transcript comprising providing a complex comprising the mRNA transcript and a sequencing engine, e.g., an RNA-dependent RNA polymerase or RNA-dependent DNA polymerase, e.g., a reverse transcriptase. The complex is immobilized in an optical confinement and a reaction mixture comprising a set of labeled nucleotides is introduced to the optical confinement. A sequencing-by-synthesis reaction is performed and a sequence of incorporation of the labeled nucleotides into a nascent polynucleotide complementary to the mRNA transcript is detected. The sequence of the mRNA transcript is determined by complementarity based upon the sequence of incorporation of nucleotides into the nascent polynucleotide. In certain embodiments, the sequencing engine is directly or indirectly bound to a surface of the optical confinement. The mRNA template can be directly or indirectly bound to a surface of the optical confinement, or can be hybridized an oligonucleotide bound to a surface of the optical confinement, e.g., at a sequence-specific region of the oligonucleotide or a poly-T region of the oligonucleotide. In certain embodiments, the mRNA transcript is circularized prior to providing the complex such that the complex comprised a circular mRNA nucleic acid and a sequencing engine. In such embodiments, the circular mRNA transcript can be repeatedly sequenced as the sequencing engine translocates around the circular template multiple times, thereby generating a linear concatemeric nascent strand comprising multiple complementary copies of the circular template.

In certain aspects, methods are provided for sequencing an RNA molecule comprising providing a complex comprising the RNA molecule and a sequencing engine and introducing to the complex a reaction mixture comprising a set of unincorporatable labeled nucleotides and a set of incorporatable unlabeled nucleotides. A sequencing-by-synthesis reaction is performed wherein only the set of incorporatable unlabeled nucleotides are incorporated into a nascent polynucleotide complementary to the RNA molecule. A sequence of associations of the set of unincorporatable labeled nucleotides with the complex is detected, and each association is indicative of complementarity of a particular unincorporatable labeled nucleotide with a particular complementary position in the RNA molecule. A sequence of the RNA molecule is determined by complementarity with the sequence of associations of the set of unincorporatable labeled nucleotides. The complex is preferably immobilized in an optical confinement. In certain embodiments, multiple associations of the set of unincorporatable labeled nucleotides with the complex are detected for every incorporation of an incorporatable unlabeled nucleotide into the nascent polynucleotide. The sequencing engine can be a wild-type sequencing engine (e.g., polymerase), an RNA-dependent RNA polymerase, or an RNA-dependent DNA polymerase (e.g., reverse transcriptase). In certain embodiments, the RNA molecule is a circular RNA molecule, and, optionally, the sequencing engine processes the circular RNA molecule multiple times during the sequencing-by-synthesis reaction. In some embodiments, the RNA molecule comprises secondary structure that is detected during the sequencing-by-synthesis reaction. In some embodiments, the RNA molecule comprises a modified or non-natural base, e.g., a pseudouridine residue or a methylated base, such as an N2-methylguanosine residue, that is detected during the sequencing-by-synthesis reaction.

In certain aspects, methods for generating redundant sequence information from a single RNA molecule are provided. In certain embodiments, such a method comprises repeatedly processing at least a portion of the single RNA molecule with a sequencing engine, wherein each time the single RNA molecule is processed at least one sequence read is generated from the portion, thereby producing multiple sequence reads from the portion, the multiple reads comprising redundant sequence information. In certain embodiments, the multiple reads are subjected to statistical analysis to determine a polynucleotide sequence of the portion of the single RNA molecule.

In other aspects, compositions for biological analyses and/or analytical reactions are provided. In certain embodiments, a composition of the invention comprises an RNA-dependent polymerase bound to an RNA template in an optical confinement, and a plurality of differentially-labeled phospholinked nucleotide analogs. In some such embodiments, the differentially-labeled phospholinked nucleotide analogs are incorporatable into a nascent polynucleotide strand during template-directed synthesis by the RNA-dependent polymerase. In alternative embodiments, the differentially-labeled phospholinked nucleotide analogs are unincorporatable into a nascent polynucleotide strand during template-directed synthesis by the RNA-dependent polymerase, and the composition optionally further comprises unlabeled phospholinked nucleotide analogs that are incorporatable into a nascent polynucleotide strand during template-directed synthesis by the RNA-dependent polymerase. In some embodiments, the RNA-dependent polymerase is a reverse transcriptase (e.g., an HIV RT) or an RNA-dependent RNA polymerase (e.g., a phi6 polymerase). The RNA template can be selected from the group comprising an mRNA, rRNA, tRNA, miRNA, piRNA, saRNA, siRNA, ribozyme, CRISPR RNA, catalytic RNA, antisense RNA, long ncRNA, or a fragment or derivative thereof. In certain preferred embodiments, the optical confinement is a zero mode waveguide.

In yet further aspects, systems for RNA sequencing are provided. In some embodiments, such systems comprise a substrate comprising a reaction site within an optical confinement, wherein a single RNA-dependent polymerase is immobilized at the reaction site and is further bound to a single RNA template molecule; a reaction mixture in contact with the reactions site comprising differentially labeled nucleotide analogs capable of incorporation into a nascent strand during template-directed polymerization by the single RNA-dependent polymerase on the single RNA template molecule; an illumination source that provides excitation illumination; an optical detector; an optical train that guides the illumination from the excitation illumination source to the reaction site and guides emission signals from the reaction site to an optical detector; and a recording device to record the emission signals detected by the optical detector.

In alternative aspects, methods for determining a nucleotide position in an RNA template are provided. In certain preferred embodiments, such methods comprise providing an immobilized complex comprising a single RNA-dependent polymerase and a single RNA template molecule; contacting the immobilized complex with a reaction mixture that comprises a set of differentially labeled nucleotides and $Ca^{2+}$ ions, and wherein the reaction mixture is deficient in $Mg^{2+}$ ions; binding one of the differentially labeled nucleotides to the immobilized complex to form a bound labeled nucleotide; and detecting an emission signal from the bound labeled nucleotide. A nucleobase in the bound labeled nucleotide is identified based at least in part on the emission signal and, by complementarity, an identity of the nucleotide position in the RNA template is determined. Optionally, the method further comprises removing the $Ca^{2+}$ ions and adding $Mg^{2+}$ ions to promote incorporation of the bound labeled nucleotide into a nascent strand complementary to the RNA template. In certain embodiments, the $Ca^{2+}$ ions are removed by addition of EGTA, and in other embodiments the $Ca^{2+}$ ions are removed by buffer exchange. Preferably, the method is repeated to promote incorporation of multiple of the differentially labeled nucleotides into the nascent strand complementary to the RNA template.

Further aspects of the invention provide diagnostic methods for viral typing. For example, a method for identifying of a specific subtype of a virus can comprise subjecting the RNA molecule to template-dependent nucleic acid synthesis reaction carried out by a single, observable polymerase enzyme, wherein at least one of the RNA molecule or the polymerase enzyme is produced by the specific subtype of the virus; monitoring nascent strand synthesis during the template-dependent nucleic acid synthesis reaction; and based on the results of the monitoring, identifying the specific subtype of the virus. For example, the results can comprise one or more polynucleotide sequences of the nascent strand that are indicative of the specific subtype of the virus. Alternatively or additionally, the results can comprise kinetic metrics for the activity of the polymerase enzyme. In certain embodiments, the RNA molecule and/or the polymerase is produced by the specific subtype of the virus, and may optionally be acquired from a sample taken from the patient infected with the specific subtype of the virus. In some embodiments, the specific subtype of the virus is a specific subtype of a virus selected from the group consisting of HIV, SARS, influenza, hepatitis B, and hepatitis C. The method can further comprise determining a treatment for a patient infected with the specific subtype of the virus.

BRIEF DESCRIPTION OF THE DRAWINGS

FIG. 2A-2B illustrates one embodiment of the RNA sequencing methods of the invention.

FIG. 4A-4B provides results from template-dependent synthesis reactions using a reverse transcriptase. FIG. 4A illustrates bulk incorporation of phospholinked dNTPs by a mutant reverse transcriptase. FIG. 4B provides a graph showing a representative time trace of fluorescence intensity from an individual ZMW during RNA-dependent DNA synthesis.

FIG. 5A-5C provides results from an analysis of the kinetics of a reverse transcriptase in the presence of unmodified nucleotides (A) and phospholinked nucleotide analogs (B). The table provides the $K_{cat}$ ($s^{-1}$) and $K_m$ ($\mu M$) for each of the four unmodified nucleotides and each of the four phospholinked nucleotide analogs (C).

FIG. 7A-7C provides results from template-dependent synthesis reactions using a reverse transcriptase and a template having an $N^2$-methylguanosine residue. The molecular structure of $N^2$-methylguanosine (A) and the location of the residue in the template (B) are provided. A plot illustrating an extended incorporation duration in the vicinity of pseudouridine is provided (C).

DETAILED DESCRIPTION OF THE INVENTION

I. General

Figure 1:
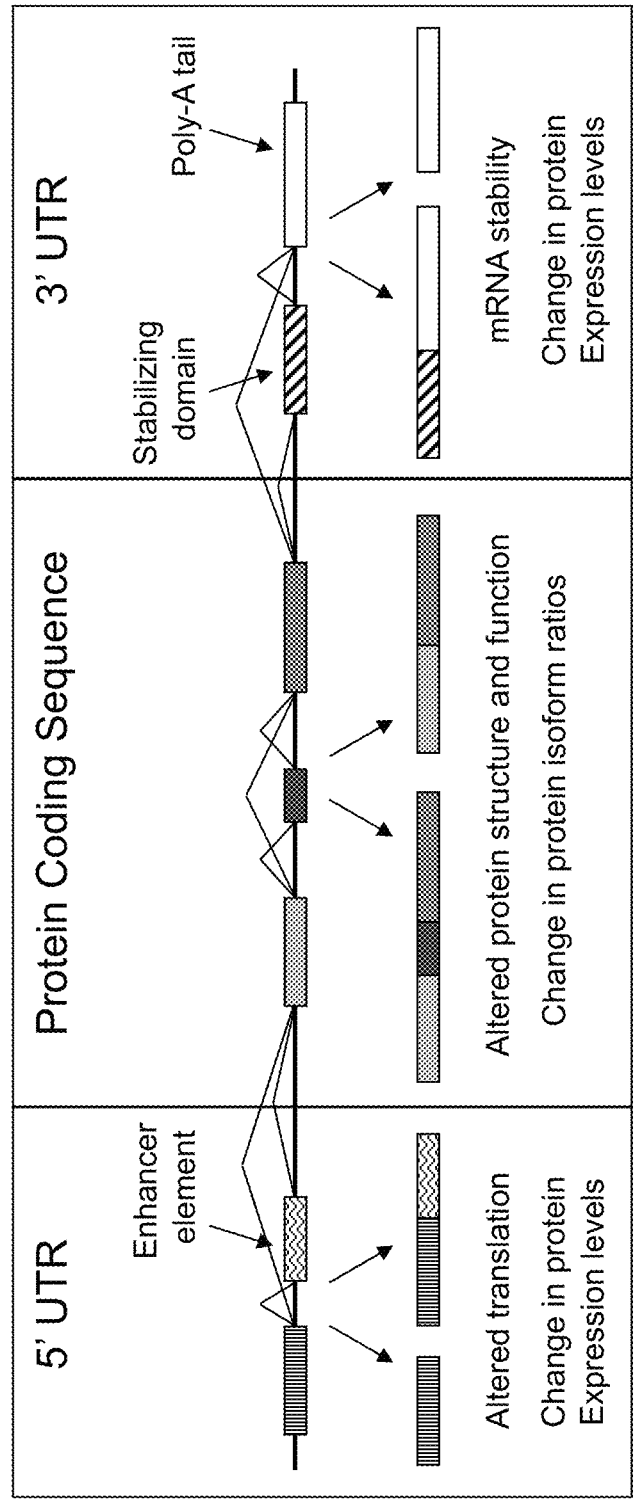
FIG. 1 illustrates the concept of "transcript splice linkage" relationships.

The present invention is generally directed to compositions, methods, and systems for performing single-molecule, real-time analysis of a nucleic acid templates, and in particular single RNA molecules. The ability to analyze such reactions in real time with single molecule resolution provides an opportunity to study those reactions as well as to potentially identify factors and/or approaches for impacting such reactions, e.g., to either enhance or inhibit such reactions.

Certain methods of the invention exploit the optical isolation properties of optical confinement techniques, such as zero mode waveguide technology, total internal reflection fluorescence (TIRF) microscopy, optical waveguide arrays, and the like. In particular, the invention provides for observation of the interaction of two or more specifically interacting reactants at the single molecule (or single molecular complex) level in order to monitor the progress of the reaction of interest. A plurality of analytical reactions may also be carried out in an array of optical confinements. Analytical reactions in an array of optical confinements can be carried out simultaneously, and may or may not be synchronized with one another.

The monitoring typically takes the form of providing the interaction with a signaling event that is characteristic of that interaction. Such a signaling event may comprise the retention of a labeled reactant within a given observation region, or the interaction of two or more interactive labeling components to produce a signal characteristic of the interaction, e.g., based upon proximity of two interacting label components. For example, in some embodiments, the labels emit optical signals that are detected by an optical detection system operably linked to a reaction site at which the analytical reaction is taking place. As used herein, a reaction site is a location on or adjacent to a substrate at which an analytical reaction is monitored, and may refer to, e.g., a position on the substrate at which one or more components of an analytical reaction are immobilized or to an effective observation volume (or "detection volume") within which an analytical reaction is monitored. The detected signals are analyzed to determine a characteristic of the analytical reaction, e.g., initiation, rate, termination, biochemical event (e.g., binding, bond cleavage, conformational change, etc.), substrate utilization, product formation, and the like. For example, characteristics of a polymerization reaction include the identity of a monomer incorporated into a growing polymer and the rate of incorporation. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In one particular example, an optically confined reaction site (also referred to as a reaction site in an "optical confinement" herein), such as a reaction site within a zero mode waveguide, is used to provide for observation of individual molecules or molecular complexes. In particular, one member of an interacting reactant pair, e.g., an enzyme, receptor, cell surface protein, ligand, substrate, nucleic acid template, or the like, is provided immobilized within an observation volume of a zero mode waveguide or waveguide array. The reactant component that interacts with the immobilized component is provided with a labeling group such that when that interactive reactant comes into contact with the immobilized reactant, the label becomes detectable (e.g., by entering the observation volume) and/or produces a detectable signal that is characteristic of the interaction.

In some cases, the characteristic signal may derive from a single label on a non-immobilized reaction component that produces a signal duration indicative of a specific interaction, e.g., as a result of binding and/or reaction with the immobilized component. For example, one may immobilize a receptor protein within the observation volume, and interrogate that receptor with a fluorescently labeled ligand. Binding of the ligand to the receptor yields an increased retention time of the fluorescent label within the observation volume. Such a signal may also or additionally be derived from a native biomolecule, e.g., the intrinsic fluorescence of a protein containing tryptophan, tyrosine, and/or phenylalanine.

Alternatively or additionally, interactive label components may be provided on different reaction components in the analytical reaction. For example, one label component can be provided on the immobilized reactant, while the other label group is provided on the non-immobilized component, or both are provided on either immobilized or non-immobilized reaction components. The different label components are selected such that when they are placed in sufficiently close proximity, such as during the interactive reaction between the two reactants, they produce a characteristic signal for that proximity, and consequently, that reaction. Alternatively or additionally, interactive label components may be provided on a single immobilized or non-immobilized reaction component that undergoes an alteration that changes the orientation of the label components (e.g., alters the distance between them) in such a way as to change the signal emitted from the labeled reaction component during its participation in the reaction. For example, Förster resonant energy transfer (FRET) labels may be employed that yield a characteristic fluorescent signal when the two components or two portions of a single component are sufficiently close to each other, such as when a substrate is bound in the active site of an enzyme, when a receptor binds to its ligand, or when a reaction component undergoes a conformational change, including but not limited to release of a portion of the reaction component.

II. Biological Analyses

The present invention is applicable to various different biological analyses and can be used to monitor single molecules (or molecular complexes) in such analyses in real time. Biological reactions comprising a molecular complex that can be immobilized in an optical confinement and one or more reaction components that can be detectably labeled and monitored in real time are particularly appropriate for monitoring and analysis in accordance with the teachings herein. Biological reactions in which a distinct detectable signal is emitted in association with a specific biochemical reaction event (e.g., incorporation, binding, stalling, dissociation, etc.) are particularly suitable.

In certain embodiments, biological processes that are monitored in accordance with the invention are polymerization reactions, and in particular nucleic acid polymerization reactions. Certain nonlimiting examples of these and other reactions include RNA-dependent DNA polymerization; RNA-dependent RNA polymerization; RNA genome analysis (genotyping, secondary structure analysis, etc.); sequencing of various different RNA species (e.g., tRNA, rRNA, mRNA, siRNA, miRNAs, etc.); and RNA splicing. While certain embodiments are described as having an RNA template, it will be understood that the compositions, methods, and systems are not limited to the use of RNA templates, and other types of templates may also be used, e.g., DNA, PNA, LNA, etc., and analogs, mimetics, and combinations thereof. Further, templates can be single-stranded, double-stranded, or may comprise both single-stranded and double-stranded portions.

Nucleic acid polymerization reactions typically involve incorporation of nucleotide monomers, such as deoxyribonucleotides, ribonucleotides, or analogs or derivatives thereof into a nascent polynucleotide strand, e.g., extending a nucleic acid primer complementary and bound to the template strand. In certain embodiments, the nucleotide monomers incorporated comprise a detectable label that identifies the type of monomer being incorporated, e.g., what nucleobase it comprises (e.g., A, T, C, G, U, and other (e.g., modified or nonnatural) nucleobases, e.g., inosine (I), thiouridine, pseudouridine, dihydrouridine, queosine, wyosine, methylated bases, artificial nucleobases used for metal base pairing (see, e.g., J. S. Lee, et al. *Biochem. Cell Biol.* 1993, 71:162-168; and K. Tanaka, et al. Science 2003, 299:1212-1213, the disclosures of which are incorporated herein by reference in their entireties for all purposes), etc.). In preferred embodiments, the label in the monomer is not incorporated into the nascent strand during incorporation, but is instead released upon incorporation, e.g., directly or indirectly linked to the polyphosphate (e.g., $PP_i$, $PPP_i$, $PPPP_i$, etc.) released by the cleavage of the phosphate chain required for incorporation. The term "phospholinked nucleotides" refers to nucleotide analogs having a detectable label attached to a phosphate group. In some embodiments, the label is directly or indirectly linked to the terminal phosphate group in the phosphate chain of the nucleotide monomer. Various nucleotide analogs that can be used with the methods described herein include those described, e.g., in U.S. Pat. No. 7,056,661; U.S. Patent Publication Nos. 20090246791 and 20090208961; and U.S. Ser. No. 12/621,352, filed Nov. 18, 2009, the disclosures of which are incorporated herein by reference in their entireties for all purposes. In addition, nucleotide monomers with other chemical modifications can also be used, e.g., nucleotides comprising a variety of leaving group chemistries, such as amino acids in the polyphosphate chain. For example, it has been shown that HIV-1 reverse transcriptase, Taq DNA polymerase, and Vent (exo-) DNA polymerase are able to process selected nucleotide analogs like amino acid dAMP phosphoramidates, e.g., L-aspartic acid phosphoramidates of deoxyadenosime, deoxyguanosine, deoxycytidine, and thymidine monophosphates (Adelfinskaya, et al. (2007) Angew. Chem. 119: 4434; Adelfinskaya, et al. (2007) Angew. Chem. Int. Ed. 46: 4356 and Adelfinskaya, et al. (2007) Nuc. Ac. Res. 35: 5060-72, the disclosures of which are incorporated herein by reference in their entireties for all purposes). Also, the incorporation of nucleotide analogs having aromatic and aliphatic structures, including an isophthalic acid derivative of deoxyadenosine 5'-O-monophosphate, have been described in Giraut, et al. (2009) Chembiochem 10(13):2246-52, the disclosure of which is incorporated herein by reference in its entirety for all purposes.

One example of a biological process that is monitored in accordance with the invention is sequencing of messenger RNA (mRNA), e.g., by observing RNA-dependent polymerization in vitro to determine sequence characteristics of an mRNA, in particular during "sequencing-by-synthesis" of a complementary DNA or RNA strand. Typically, such reactions comprise an mRNA molecule (template) complexed with an RNA-dependent polymerase sequencing "engine" (e.g., an RNA-dependent RNA polymerase, a DNA polymerase with RNA-dependent polymerization activity, or a reverse transcriptase (RT)) in the presence of a set of labeled nucleotides and other components required for mRNA-template-dependent polymerization. In particularly preferred embodiments, such reactions provide real-time monitoring of nucleotide incorporation into a single nascent polynucleotide chain (e.g., DNA or RNA) complementary to a single mRNA template as it is processed by a single polymerizing enzyme in a processive polymerization reaction. In some such methods, an enzyme with reverse transcriptase activity (e.g., a reverse transcriptase or a DNA polymerase with reverse transcriptase activity) in complex with an mRNA template is immobilized on a substrate (e.g., in an optical confinement) and detection of nucleotides incorporated into a complementary DNA strand is monitored in real time. In certain preferred embodiments, such a reaction allows detection of an incorporation event on a single complex on a substrate to be distinct from an incorporation event on any other complex on the substrate. A signal indicative of an incorporation event may be an emission from a label associated with reaction component, e.g., a label bound to a nucleotide that is released if the nucleotide is incorporated into the complementary DNA strand. Detection and analysis of a series of signals from a single complex provides information about the sequence of the nucleotides incorporated into the nascent complementary strand. In certain preferred embodiments, each type of nucleotide (e.g., A, T, C, G, U, and others known in the art) is differentially labeled, allowing incorporation of each type of nucleotide to be detected and discriminated from incorporation of every other type of nucleotide, thereby providing a nucleotide sequence of the complementary strand. In certain preferred embodiments, such methods do not require amplification of the mRNA template prior to analysis.

Such compositions, methods, and systems enable new scientific research on mRNA processing and maturation, for example, by determining the composition of transcriptomes, e.g., for cells or tissues of interest. Transcriptomes are the sets of all mRNA transcripts present in living cells, e.g., at a given time or under a given set of conditions. The transcriptome for a given cell type of interest can be determined by subjecting whole cell (total) mRNA to an RNA-dependent polymerization reaction and monitoring the incorporation of nucleotides in real time to determine the sequences of all mRNAs present in the cell. In this way, different cell types can be compared to one another to identify differences in their individual transcriptomes, e.g., mutant vs. wild-type, one strain versus another, diseased versus healthy, etc. In certain embodiments, the relative amounts of only one type or a subset of types of mRNAs in different cells or tissues is sought, and in those cases the specific mRNA(s) can be targeted for sequencing in various ways. For example, primers specific for (e.g., that hybridize to) only those mRNAs of interest can be included in a reaction using a polymerase that requires a primer to initiate synthesis, or whole mRNA from a culture of a defined cell concentration (e.g., based on optical density) could be treated to remove mRNAs that are not of interest, e.g., by affinity column chromatography. These and other methods of enriching an mRNA population for target mRNAs are further described below.

Such studies can provide information related to the biological bases for phenotypic differences between different cell types. Further, the compositions, methods, and systems provide new types of drug-screening assays, e.g., that monitor the effect(s) of drugs and other agents on transcriptome composition or RNA-dependent polymerization. For example, mRNA from cells exposed to a drug under investigation can be sequenced to provide a set of mRNAs present in the cells in the presence of the drug. Likewise, mRNA from cells can be sequenced to provide a set of mRNAs present in the cells in the absence of the drug. Differences between the mRNAs present in the cells in the presence and absence of the drug provide information on the impact of the drug on RNA metabolism in the cells and can be used to screen for drugs that have specific desired impacts on particular mRNAs in the cell. Further, basic scientific research can be performed on the processivity of polymerization at the single-molecule level under different reaction conditions and/or in the presence of various agents, e.g., changes in fidelity, rate, etc., and can thereby function as a drug discovery tool, for example, for diseases that require reverse transcriptase activity (e.g., HIV/AIDS). In particular, many drugs for HIV/AIDS target HIV reverse transcriptase, and the present methods provide methods for studying the effects of these drugs in real time, optionally with single molecule resolution. Use of the methods, compositions, and systems provided herein for in vitro monitoring of RNA-dependent polymerization are further described below. In related embodiments, other types of RNA molecules can also be characterized by "cDNA sequencing-by-synthesis," e.g., catalytic RNAs, siRNA, saRNA, microRNA (miRNA), piRNA, CRISPR RNA, antisense RNA, long noncoding RNA, tRNA, rRNA, etc.

As noted repeatedly above, the methods and systems provided herein can be used for testing the effects of various agents on an in vitro biological reaction. Such agents may be drug candidates and the methods would constitute a pharmaceutical screening method for a given in vitro model system. For example, the ongoing biological reactions could be monitored in real time at a single-molecule (or single-molecular complex) level for various kinds of affects, including but not limited to rate, processivity, fidelity, ligand preference, binding duration, interpulse duration, error metrics, and various other aspects specific for a particular biological reaction of interest. Further, these assays can be incorporated into diagnostic kits for preparing and/or carrying out such reactions, e.g., in a home, laboratory, or clinical setting.

III. Transcriptome Sequencing

The sets of all mRNA transcripts present in living cells, termed "transcriptomes," are fundamental units for regulating life processes. The direct and comprehensive determination of their sequence content is essential for improving our understanding of proteome constitution and flexibility, thereby providing the knowledge and targets to intervene in such diverse processes as cancer, tissue specificity, (auto)immune responses, genetic diseases, and environmental adaptation, to name but a few. The present invention provides direct and full-length sequencing of mRNA transcripts, which was not previously feasible due to the lack of an enabling technology.

Unlike the determination of whole genomes, transcriptome analysis has proved a difficult experimental task because, unlike DNA, mRNA transcripts in cells are present in highly uneven abundance and are variable in a context and environmentally sensitive manner. Therefore, RNA sequence information obtained conventionally by labor-intensive sequencing of expressed sequence tags (ESTs) and complementary DNA (cDNA) libraries has thus far resulted in only a handful of transcriptomes being extensively characterized (see, e.g., Y. Lee, et al., Nucleic Acids Res 2005, 33, D71, which is incorporated herein by reference in its entirety for all purposes).

Recently, improved DNA sequencing technologies have opened new approaches to transcriptome studies. While a number of these emerging studies were dependent on existing genome annotations (see, e.g., N. Cloonan, et al., Nat Methods 2008, 5, 613; A. Mortazavi, et al., Nat Methods 2008, 5, 621; U. Nagalakshmi, et al., Science 2008, 320, 1344; K. Salehi-Ashtiani, et al., Nat Methods 2008, 5, 597; and B. T. Wilhelm, et al., Nature 2008, 453, 1239, all of which are incorporated herein by reference in their entireties for all purposes), very recently the yeast transcriptome was determined ab initio, i.e. based only on the unannotated genome sequence, using conventional cDNA conversion and massively parallel, short-read DNA sequencing technology (M. Yassour, et al., Proc Natl Acad Sci USA 2009, 106, 3264, which is incorporated herein by reference in its entirety for all purposes). Using just one method and in a matter of only days, this study identified most regions of coding and noncoding RNA transcripts with their boundaries, splice junctions and variants, and posttranscriptional modifications. Despite these important scientific and technological achievements, several limitations were recognized by the authors. Sample preparation steps, such as cDNA generation, shearing, amplification and sequencing adapter ligation can introduce errors with respect to sequence and biasing mRNA concentrations. Because sequencing was limited to very short reads (e.g, 36 bases in this study), transcript identification was limited to alignable (non-repetitive) genomic regions. In addition, due to this short readlength, 23% of all reads had to be discarded because they mapped to more than one genomic locus. Further, ~25% of all reads could not be mapped to any genomic locus, largely due to position-specific sequencing errors and, to some extent, splice junction reads. 13% of genes could not be confidently connected due to gaps or unevenness in coverage, although the authors conclude that these assignments could likely be largely resolved in the future by utilizing "paired-end" reads (see, e.g., M. J. Fullwood, et al., Genome Res 2009, 19, 521, which is incorporated herein by reference in its entirety for all purposes). Limitations of short RNA sequencing reads with respect to determining transcript boundaries in highly compact genomes were also recognized. For example, 8-21 nucleotides are missing at the 5'-end of the transcript due to the study's sample preparation protocol (J. M. D'Alessio, et al., Nucleic Acids Res 1988, 16, 1999, which is incorporated herein by reference in its entirety for all purposes).

These difficulties compromise the confidence in full-length transcripts assignments, absolute expression levels, splice locations and isoforms, and sensitivity to the presence of rare transcripts. Problems are exacerbated in organisms with less compact genomes than yeast. Alternative splicing (estimated at 74% of all human genes (see K. Salehi-Ashtiani, et al., incorporated herein above) is used frequently for increasing the size and flexibility of the proteome in different tissues and in response to various environmental factors (see, e.g., W. Zhang, et al., Hum Genet 2009, 125, 81, which is incorporated by reference in its entirety for all purposes). The human genome has an average number of 9 exons per gene, resulting in an average of 6 different mRNAs per loci (see, e.g., E. Birney, et al., Nature 2007, 447, 799; and M. K. Sakharkar, et al., In Silico Biol 2004, 4, 387, both of which are incorporated herein by reference in their entireties for all purposes). Projected increases in read lengths by second generation DNA sequencing technologies to ~100 bases will not be sufficient to elucidate these complexities (e.g., at 100 base read length, only 80% of gene structures are assembled correctly, despite 20-fold coverage (see N. Cloonan, et al., incorporated herein above).

Addressing these shortcomings by more direct, full-length sequencing of mRNA is therefore highly desirable. Reaching the ultimate limit of single transcript molecule sensitivity will enable discoveries of currently inaccessible biological relationships. As an example, FIG. 1 illustrates the concept of "transcript splice linkage" relationships. In conventional sequencing such as in the methods mentioned above, many sequencing reads yield average values for relative abundances of exons, but the molecular connectivities are generally hidden from such ensemble molecule measurements. Regulatory processes by which certain splice isoforms are linked in a response to certain environmental or gene regulation stimuli are masked. This is particularly prevalent in genes involved in immunological responses, where thousands of different mRNA variants are possible from a single gene, either by genetic recombination or by alternative splicing (see, e.g., S. Spicuglia, et al., Curr Opin Immunol 2006, 18, 158; and F. L. Watson, et al., Science 2005, 309, 1874, both of which are incorporated herein by reference in their entireties for all purposes). Full-length transcript sequencing will be essential to unequivocally characterize mRNA from such loci.

In certain aspects, the present invention provides direct and full-length sequencing of mRNA transcripts through a technology that involves observing the activities of single molecules of RNA-dependent polymerases in real time and with high multiplex, thereby sequencing mRNA transcripts with high throughput. In preferred embodiments, one or more components of the sequencing reaction are immobilized on a substrate, e.g., in an optical confinement such as, but not limited to, a zero mode waveguide (ZMW), as described below. For example, one or more of an enzyme, template, or primer may be bound, directly or indirectly to a reaction site. In certain embodiments, a template is indirectly bound through hybridization with a complementary oligonucleotide immobilized at the reaction site. The transformative potential of fast and economical transcriptome analysis is vast, and such a technology can be commercialized for research and diagnostic applications.

In certain aspects, the present invention provides methods and systems for the analysis of RNA sequences and particularly for the analysis of transcriptomes directly and in high throughput by full-length sequencing of individual mRNA transcript molecules. In particular, the invention employs analogous processes used for single-molecule, real-time DNA sequencing, and, with some modifications, exploits such processes in the present invention. Such DNA sequencing technology has been previously described in, e.g., U.S. Pat. No. 7,056,661 and Eid et al., (2009) Science 323:133-138, the full disclosures of which are incorporated herein by reference in their entireties for all purposes. As will be appreciated upon reading the instant disclosure, the impact of the present invention is expected to be pervasive in biology and medicine. Comprehensive and quantitative analysis of mRNA enabled by the methods and systems of the invention are expected to become a new method of choice for characterizing biological states. By way of example, for many applications it will prove more informative to sequence mRNA rather than DNA because the transcriptome will additionally inform about the organism's "health" state.

While primarily described in terms of the analysis of transcriptomes, it will be appreciated that the methods and systems described herein are equally applicable to other research and application areas, e.g. rapid and cost-effective sequencing of RNA viruses, non-coding RNA (e.g., catalytic RNAs, siRNA, saRNA, microRNA (miRNA), piRNA, CRISPR RNA, antisense RNA, tRNA, rRNA, etc.) and retrotransposon characterization, or detailed kinetic studies on HIV reverse transcriptase, a major drug screening target in the fight against AIDS, as described in greater detail below.

As noted previously, there has been developed a method for real-time sequencing of single DNA molecules (see Eid et al., incorporated above), with intrinsic sequencing rates of several bases per second and average read lengths in the kilobase range. In accordance with the present invention, direct RNA sequencing is carried out in a conceptually similar approach by eavesdropping on the activity of enzymes carrying out RNA template-directed polymerization. Sequential base additions catalyzed by the enzyme into the growing complementary nucleic acid strand are detected as they are incorporated, e.g., using fluorescently-labeled nucleotides or other applicable methods. Carried out in a highly parallel operational mode, transcriptomes are sequenced by essentially "watching", with base-pair resolution, what normally constitutes the first step of a cDNA library preparation protocol.

Accordingly, the RNA sequencing methods and systems of the invention harness the intrinsic power of RNA-dependent polymerase enzymes as sequencing engines, allowing their speed, processivity, efficiency, and fidelity to be exploited directly. Full-length sequences are obtained from single mRNA transcripts. This contrasts other current techniques in which the molecular integrity of RNA is destroyed during the course of sequencing fragment generation by shearing or digestion. The generation of sequence-ready cDNA libraries before sequencing is unnecessary, saving labor and time, and avoiding shortcomings with respect to bias and errors introduced during conventional preparation methods.

As with single-molecule real-time DNA sequencing methods described above, the long continuous sequence reads greatly simplify the downstream bioinformatics for genome analysis in the context of structural and copy number variation. For the first time, transcript assignments from low complexity genomic regions are permitted. Detailed alternative splicing mRNA population maps, especially important in cancer biology where differential gene expression and splice isoforms leading to pathological states may not be captured in current genome annotation databases, are obtainable. One embodiment of the RNA sequencing methods of the invention is illustrated in FIG. 2. Two technology components that are used in certain preferred embodiments of this process are (i) zero-mode waveguide (ZMW) confinement technology that allows single-molecule detection at concentrations of labeled nucleotides relevant to the enzyme, and (ii) phospholinked nucleotides that facilitate observation of uninterrupted polymerization in real time.

In certain embodiments, ZMW nanostructures are provided (FIG. 2A). Dense arrays of these nanostructures 205, ~100 nm in diameter, are fabricated in a ~100 nm metal film 210 deposited on a transparent substrate 215 (e.g., silicon dioxide) (see, e.g., M. Foquet, et al., *J. Appl. Phys.* 2008, 103, 034301 and M. J. Levene, et al., *Science* 2003, 299, 682, both of which are incorporated herein by reference in their entireties for all purposes). Each ZMW becomes a nanophotonic visualization chamber for recording an individual polymerization reaction, providing a detection volume of just 100 zeptoliters ($10^{-21}$ liters). This volume represents a ~1000-fold improvement over diffraction-limited confocal microscopy, making it possible to observe single incorporation events against the background created by the relatively high concentration of fluorescently labeled nucleotides.

Figure 2B:
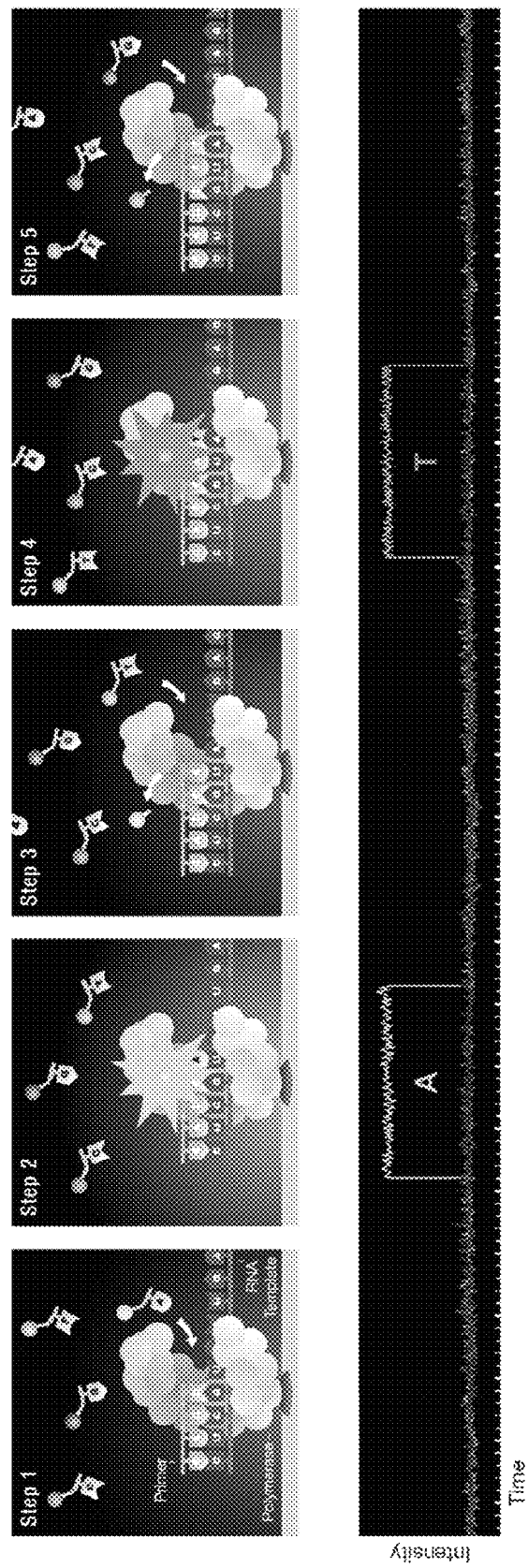

Also as shown, phospholinked deoxyribonucleotides 220 (or ribonucleotides for embodiments using an RNA-dependent RNA polymerase) for which the fluorescent label is attached to the terminal phosphate rather than the base are typically employed as the labeled nucleotide. 100% replacement of unmodified nucleotides by phospholinked nucleotides in the reaction mixture is facilitated by cleavage of the fluorophore by the enzyme 225 as part of the incorporation process, which generates a completely natural, double-stranded nucleic acid product 230. Each of the four different nucleobases is labeled with a distinct fluorophore to discriminate base identities during incorporation events, thus enabling sequence determination of the complementary RNA template 235. During incorporation, the enzyme 225 holds the labeled nucleotide in the ZMW's detection volume for tens of milliseconds, orders of magnitude longer than the average diffusing nucleotide is present. Fluorescence is emitted continuously from the fluorophore label during incorporation, causing a detectable pulse of increased fluorescence 240 in the corresponding color channel. The pulse is terminated naturally by the polymerase releasing the pyrophosphate-linker-fluorophore group. The polymerase then translocates to the next base, and the process repeats. FIG. 2B provides a step-by-step diagram of the incorporation process. As such, in preferred embodiments the polymerase proceeds in a processive manner, repeatedly incorporating nucleotides into the nascent nucleic acid strand without the need for experimental manipulations by the investigator, e.g., removal of blocking groups, buffer exchange, and the like, such as those required in certain "flush-and-scan" methods. (See, e.g., Ozsolak, et al. (2009) Nature 461:814-819, which is incorporated by reference herein in its entirety for all purposes.) In this way, a single polymerase enzyme molecule is monitored in real-time as it processes a single template nucleic acid molecule and individual incorporation events wherein nucleotides are incorporated into a complementary nascent strand are detected as they occur. Signals detected that are indicative of incorporation are recorded and analyzed to determine a polynucleotide sequence of the nascent strand, and by complementarity, a polynucleotide sequence of the template strand.

In preferred aspects, direct RNA sequencing is carried out by immobilizing the polymerase enzyme within the observation or illumination volume 245 of a reaction site, e.g. a ZMW (FIG. 2A). In this mode of operation, it is the experimental processivity of the enzyme that determines the sequence read length. As such, in such preferred aspects, RNA-dependent polymerases with high intrinsic processivities (see, e.g., A. Bibillo, et al., *J Biol Chem* 2002, 277, 34836; and D. S. Gregerson, et al., *Biochemistry* 1980, 19, 301, which are incorporated herein by reference in their entireties for all purposes) will generally be preferred. Immobilization of enzymes may employ any of a variety of techniques, including, for example, in vivo biotinylation of a N- or C-terminal peptide tag on the protein (e.g. AviTag (Avidity)) (see, e.g., D. Beckett, et al., *Protein Sci* 1999, 8, 921, which is incorporated herein by reference in its entirety for all purposes), which provides high efficiency of biotinylation and preservation of enzymatic activities. A variety of other surface treatments are also optionally exploited to avoid non-specific interactions of free reagents and the surfaces of the illumination volume, which could give rise to aberrant signals. For example, polyphosphonate and silane-based surface coatings may be exploited that mediate enzyme attachment to the transparent floor of the ZMW while blocking non-specific attachments to the metal top and side wall surfaces (see, e.g., J. Eid, et al. (incorporated herein above) and J. Korlach, et al., *Proc Natl Acad Sci USA* 2008, 105, 1176, which is incorporated herein by reference in its entirety for all purposes). In addition, long templates may be loaded in ZMWs and subjected to sequencing-by-synthesis, thereby generating kilobases of RNA sequence from these templates (J. Korlach, et al., incorporated herein above).

Single-molecule sequencing reactions can be carried out on highly multiplexed confocal fluorescence microscopy systems (see, e.g., P. M. Lundquist, et al., *Optics Letters* 2008, 33, 1026, which is incorporated herein by reference in its entirety for all purposes), in which the instrument detects fluorescence signals from an array of thousands of reaction sites, e.g., ZMWs, simultaneously, resulting in a highly parallel operation. System temperatures are configured for optimal reaction conditions including temperatures of up to 50° C. or higher. For example, on a ZMW array each ZMW, separated from others by distances of a few micrometers, represents an isolated sequencing chamber. The overall RNA sequencing throughput of the method will generally vary depending upon a variety of several system performance characteristics. For example, assuming a system multiplex of 3,000 ZMWs, an efficiency of loading ZMWs with single polymerase/template complexes of ~30% (Eid, et al. and J. Korlach, et al., both incorporated herein above), an average speed of polymerization of ~10 bases/s (well below the maximum elongation rate of, e.g. AMV RT or R2 RT (see, e.g., A. Bibillo, et al., incorporated herein above)) and a system efficiency of measurement time vs. chip loading and alignment time of 80%, the overall raw sequencing output would be ~26 Megabases/hour, equivalent to ~2× coverage of the full-length transcriptome of budding yeast (see M. Yassour, et al., incorporated herein above; and L. M. Hereford, et al., *Cell* 1977, 10, 453, incorporated herein by reference in its entirety for all purposes). This throughput of ~4 GB of sequencing reads over a 14 day time period exceeds the ~1.3 GB of sequence reads acquired on an Illumina Genome Analyzer System over the same time period used for the yeast transcriptome construction study (see M. Yassour, et al., incorporated herein above), although the partitioning of time necessary for RNA extraction, library preparation and actual sequencing was not specified in Yassour, et al. Higher throughput systems, e.g., having significantly higher multiplexing capabilities, higher loading yields, etc. will have significant impacts upon the overall throughput.

Primers for use with the instant invention can comprise deoxyribonucleotides, ribonucleotides, and analogs, mimetics, derivatives, and combinations thereof. In certain embodiments, an RNA template comprises a terminal portion that forms a hairpin structure for priming synthesis of the complementary strand. Primers may be immobilized at a reaction site, or may be present free in solution and/or in complex with a polymerase and/or template nucleic acid. In certain embodiments, a primer is not required, e.g. when a polymerase capable of primer-independent synthesis is used.

Polymerases for use with the instant invention may synthesize a nascent strand comprising RNA or DNA. In certain preferred embodiments, a polymerase is used that is capable of strand displacement, e.g. M-MLV, phi6, and phi29. Strand displacement activity is particularly relevant where secondary and/or tertiary structure is present within the RNA template at a level that impedes synthesis of a complementary strand by a polymerase not capable of strand displacement. Alternatively, or in addition, reaction conditions can be modified to remove or weaken secondary and/or tertiary structures in the template, e.g., by increasing the reaction temperature, changing the pH, or addition of destabilizing agents, e.g., urea, low molecular weight amides, sulfoxides, betaines, polyamines, primers that disrupt secondary structure, etc. Further, a polymerase is preferably a processive polymerase that can incorporate hundreds or thousands of nucleotides into a nascent strand without dissociation. In certain embodiments, a polymerase and/or the template nucleic acid is immobilized at a reaction site, e.g., via a linkage to a solid support. In certain embodiments, both the polymerase and the template nucleic acid are immobilized at the reaction, and this arrangement is especially useful when a polymerase is used that has low processivity since immobilization of both at the reaction site increases the likelihood that the polymerase will rebind to the template and reinitiate synthesis after dissociation.

Although the methods provided herein describe sequencing of an RNA template in a position-by-position manner, in certain embodiments a full or error-free sequence is not required to identify a given RNA template. For example, comparison of an incomplete or error-containing sequence read to a known sequence can be performed and a likelihood that the sequence read is the same as the known sequence can be determined. Given the likelihood, it is determined whether the sequence read is from the same template as is represented by the known sequence. In other words, if expression of a known mRNA is being tested by performing transcriptome analysis of whole RNA from a given cell or culture, a sequence read so generated need only provide enough information to inform the ordinary practitioner whether the known mRNA is being transcribed.

In particularly preferred aspects, direct incorporation of labeled phospholinked nucleotides represents the most efficient operational mode of this RNA sequencing method. Alternatively, with the high sensitivity of single-molecule detection instrument, RNA sequence information could also be obtained by detecting just the binding events of phospholinked nucleotides in the active site, without subsequent catalysis by the enzyme, e.g., in the case of phospholinked nucleotides that are not incorporatable by the polymerase, e.g., due to a non-cleavable bond between the alpha and beta phosphate groups of the nucleotides or other modifications rendering the nucleotides chemically unincorporatable, the presence of a blocking group at the 3' end of the primer, the absence of reaction components (e.g., divalent cations) that are required for incorporation, the presence of non-catalytic metal ions (e.g., $Ca^{2+}$, $Sr^{2+}$, $Ba^{2+}$, $Zn^{2+}$, etc.), and the like. This repetitive "sampling" of the active site by the cognate labeled nucleotide (also referred to as "cognate sampling") would be detected via fluorescence pulses. Methods of sequence analysis using cognate sampling are further described in U.S. Ser. No. 12/584,481, filed Sep. 4, 2009, and incorporated herein by reference in its entirety for all purposes.

Cognate sampling can, in some embodiments, be followed by the eventual incorporation of a nucleotide. For example, reaction conditions that allow sampling but not incorporation can be changed to allow incorporation of nucleotides that were previously unincorporatable, e.g., due to a missing reaction component, such as a divalent cation. In some embodiments, the incorporation event post-sampling is limited to one nucleotide, e.g., by virtue of a blocking group incorporated into the nucleotide finally incorporated. For example, after allowing cognate sampling under conditions that do not permit incorporation ("sampling conditions"), the reaction conditions are modified to allow incorporation, but because the nucleotide analogs comprise blocking groups that prevent further primer extension, only one nucleotide analog is incorporated. Following detection of incorporation, the sampling conditions are restored, e.g., by buffer exchange, and the blocking group is subsequently removed, thereby allowing sampling of nucleotide analogs complementary to the next position of the template. The process can be repeated to generate a nascent strand of a desired length.

In embodiments in which a sampled nucleotide comprises a modification that does not permit incorporation by the polymerase, a labeled or unlabeled nucleotide that does not comprise the modification can be incorporated. For example, such an unmodified nucleotide can be added to the reaction mixture during the reaction, or can be present in the solution with the modified nucleotide, e.g., at a lower concentration. The concentration of the incorporatable nucleotide analog can be adjusted to promote a desired average number of sampling events prior to incorporation. After incorporation, the polymerase translocates to the next position and the cycle begins again.

The sequence of repetitive associations of complementary unincorporatable nucleotides with the polymerase complex is complementary to the sequence of the RNA template, and the data so generated is subjected to statistical analysis to produce sequence "reads" for both the nascent polynucleotide and, by complementarity, for the RNA template. The ratio of labeled to unlabeled nucleotides can be tuned to adjust the number of phospholinked active-site sampling events before incorporation and translocation to the next base occurs. Further, statistical analysis of various metrics can distinguish between the incorporation of a single nucleotide and multiple incorporations of identical nucleotides (homonucleotide repeats). For example, the average number of sampling events (or "pulses") per incorporation event follows an exponential distribution such that incorporation of one nucleotide can be distinguished from incorporation of multiple identical nucleotides, so the distribution and/or average number of pulses at a given location on a template is indicative of the number of identical nucleotides incorporated into the complementary strand. Alternatively or additionally, the total time for a polymerase to pass through a homonucleotide repeat is also indicative of the number of identical nucleotides in the repeat such that the distribution and/or average time it takes for a polymerase to complete incorporation of one type of nucleotide is indicative of the number of identical nucleotides incorporated into the complementary strand. The reaction conditions and/or choice of polymerase can be adjusted to accentuate these behaviors and, thereby, facilitate determination of the sequence of nucleotides incorporated into a newly synthesized nucleic acid, for example, conditions that favor cognate sampling over incorporation and conditions that slow the rate of incorporation. Various methods for modifying reaction conditions and/or enzymes to affect enzyme kinetics are provided, e.g., in U.S. Patent Publication No. 2010/0047802; U.S. patent application Ser. No. 12/584,481, filed Sep. 4, 2009; and U.S. patent application Ser. No. 12/384,112, filed Mar. 30, 2009, the disclosures of which are incorporated herein by reference in their entireties for all purposes.

These strategies are not limited to phospholinked nucleotides, but are also compatible with other types of fluorescence-tagged nucleotides, such as the common base-linked nucleotides. The advantages of this approach include the use of unmodified or wild-type enzymes (e.g., enzymes that naturally incorporate only unlabeled nucleotides) and their optimal reaction conditions; the flexibility of adjusting the ratio of phospholinked to native dNTPs to determine the average number of pulses per incorporation event; and the redundancy of signal to decrease the incidence of a missed base incorporation. (A related method particularly suitable for sequencing DNA templates is provided in U.S. Ser. No. 12/370,472, filed Feb. 12, 2009, which is incorporated herein by reference in its entirety for all purposes, certain aspects of which are equally applicable to the instant invention.) Drawbacks of this sequencing strategy include (i) a lower overall sequencing speed because each incorporation event is preceded by a time period of active-site sampling for base identity detection, and (ii) potential challenges to detect homonucleotide repeats in the RNA template, in case incorporations of unmodified nucleotides occur rapidly and do not produce a recognizable gap between like-colored pulse groups. The latter challenge can be overcome by slowing the release and/or translocation steps, thereby enhancing the gap created between pulses to signify an incorporation event, or limiting the incorporation event to one nucleotide at a time, as described above. Various methods for slowing the translocation step in a nucleic acid synthesis reaction are provided in, e.g., in U.S. Ser. Nos. 12/414,191 and 12/384,112, both filed Mar. 30, 2009; U.S. Ser. No. 12/537,130, filed Aug. 6, 2009; and U.S. Ser. No. 12/584,481, filed Sep. 4, 2009, the disclosures of all of which are incorporated herein by reference in their entireties for all purposes. Such methods include changing various components of the reaction mixture (e.g., concentrations of certain divalent cations) and using mutant enzymes that have a slow and/or "two-step" phenotype.

IV. Analysis of Enzyme Kinetics

In addition to nucleotide sequence information for an RNA template, the invention also provides a means for monitoring the activity of a single polymerase in real time with single-molecule resolution. Various aspects of enzyme activity can be monitored, including but not limited to rate, fidelity, time per incorporation, incorporation duration, pausing, error profiles, time between incorporation initiations, residence time, time between release of polyphosphate and binding of subsequently incorporated nucleotide, and the like. For example, detailed kinetic studies can be performed on RNA-dependent polymerases during nascent strand synthesis under different conditions (e.g., presence of different divalent cations or mixtures thereof) and in the presence of various agents, e.g., drug candidates. In preferred embodiments, these assays are performed at single-molecule resolution in real-time. Further, such studies will provide valuable information on the basic kinetics of the polymerase, that this knowledge can be used to design conditions that modulate enzyme activity, e.g., rate, fidelity, pausing, etc. for various different types of analytical reactions. Of particular interest is human immunodeficiency virus (HIV), a lentivirus known to cause acquired immunodeficiency syndrome (AIDS). The virus encodes a reverse transcriptase (HIV RT) that is involved in the conversion of the viral RNA genome to double-stranded DNA so it can be subsequently integrated into the host genome. Given the widespread occurrence of HIV/AIDS, much research is directed to its prevention and treatment, and HIV RT is one of the major drug screening targets. In fact, many HIV/AIDS drugs work directly to inhibit or block the HIV RT, and the present invention provides a new method for studying the kinetics of HIV reverse transcriptase, and for identifying agents that alter those kinetics, which may be used to develop new treatments for those infected with the virus. Although HIV RT is specifically included in the descriptions of certain embodiments of the invention, it will be understood that the methods provided herein are not limited to this enzyme and are also applicable to other polymerase enzymes. For example, they can be applied to the study those isolated from RNA viruses and retroviruses that cause other human diseases, e.g., SARS, influenza, hepatitis B, and hepatitis C, as well as viruses that are harmful to other organisms, e.g., plants and animals grown for food production, e.g., Rous sarcoma virus and Cauliflower mosaic virus.

The kinetics of nascent strand synthesis can also be studied under various reaction conditions, e.g., by modulating the presence/concentration of various divalent cations. Various methods for condition-dependent modulation of polymerase activity has been described previously, e.g., in U.S. Patent Publication No. 2009/0286245 (incorporated herein by reference in its entirety for all purposes), and these methods may also be applied to RNA-dependent polymerase enzymes in the context of the present invention. For example, although HIV RT works well in the presence of $Mg^{2'}$, its kinetics can be modulated with mixtures of various divalent cations, e.g., $Mg^{2+}$, $Mn^{2+}$, and/or $Ca^{2+}$. (See, e.g., Tan, et al. (1991) Biochemistry 30(10):2651-5, incorporated herein by reference in its entirety for all purposes.) For example, in certain embodiments a "flush and scan" strategy for RNA sequencing comprises addition of labeled nucleotides in the presence of $Ca^{2+}$ to form a stable ternary complex of a primed RNA template, a reverse transcriptase, and a nucleotide to be next incorporated into a nascent strand (e.g., complementary to the nucleotide of the template strand that is in the active site of the enzyme.) Such a ternary complex does not comprise other non-complementary nucleotides in the reaction mixture. The ternary complex formed can be detected and the identity of the bound nucleotide (e.g., A, G, T, or C) determined. The $Ca^{2+}$ is subsequently removed, $Mg^{2+}$ is added, and incorporation of the bound nucleotide occurs. Removal of $Ca^{2+}$ can be accomplished by various methods including, e.g. washing and/or addition of a chelating agent. For example, EGTA (ethylene glycol tetraacetic acid) has a much higher affinity for $Ca^{2+}$ ions than $Mg^{2+}$ ions, and can be used to effectively "remove" them from the reaction mixture. In certain embodiments, the unbound nucleotides present in the reaction mixture are removed, e.g. by washing, prior to addition of $Mg^{2+}$, and the $Mg^{2+}$ is added in the absence of nucleotides to allow for elongation of the nascent strand by only one nucleotide position. The cycle is repeated for each nucleotide position to be sequenced. In certain embodiments, each type of nucleotide is labeled with the same detectable moiety, and each is introduced to the primed RNA template and reverse transcriptase separately. A constant or stable signal from the reaction site is indicative that a complementary nucleotide has bound to the complex, and the identity of that nucleotide is known based on the order of addition of the nucleotides to the reaction mixture. The complex is washed and $Mg^{2+}$ is added to promote incorporation of the complementary nucleotide in the absence of other nucleotides. If the unbound nucleotides are not removed, multiple may be incorporated in the presence of $Mg^{2+}$, e.g., if there is a homopolymer region in the template. Such a lack of resolution is acceptable in certain sequencing reactions, e.g. those seeking to simply identify or genotype a template may not require full sequencing to accomplish their aim. The cycle is repeated for each position to be sequenced. Alternatively, each type of nucleotide can be differentially labeled so the emission signal from the label is indicative of the type of nucleotide, and all labeled nucleotides can be present in the reaction mixture simultaneously. In further embodiments, reversible terminators on the 3'-OH of the nucleotides could be used to limit incorporation to one nucleotide without the need for removing other nucleotides from the reaction mixture prior to adding $Mg^{2+}$. Such reactions can be monitored at the single molecule level, or can be monitored in a bulk or multimolecular format. Further, the reactions can be performed using various experimental platforms, including but not limited to microtiter plate surfaces, arrays, chips, TIRF, FCS, epifluorescence microscopy, zero-mode waveguides, optical waveguide substrates, and the like. In some embodiments, such as genotyping of a single base position in genomic DNA, or typing of viral genomes, only a single binding event need be detected to identify the sample template. The conditions necessary for ternary complex formation need not be changed to permit incorporation, since the detection of the ternary complex in the absence of actual incorporation is sufficient to identify the complementary base in the template, whether all nucleotides are simultaneously present and differentially labeled, or if each is introduced to the polymerase separately.

The invention provides methods not only for determining a nucleotide sequence of an RNA template, but also for determination of base modifications and/or secondary structure of the RNA template. The importance of base modifications and secondary structure in RNA function, regulation, and metabolism cannot be understated. For example, the secondary structure of RNA molecules (e.g., mRNA, rRNA, tRNA, miRNA, siRNA, piRNA, long ncRNA, etc.) is important for transcriptional regulation, translational control, RNA interference, the function of riboswitches and other cis-regulatory elements, and splicing and other post-transcriptional modifications of RNA species, e.g., nucleobase modifications, which are also known to have regulatory roles, including in some cases formation and/or stabilization of secondary structure. In certain preferred embodiments, an energetic profile of the polymerase processing the RNA template is generated that is a direct reflection of the secondary structure of the RNA template, e.g., where the dynamics of the polymerase are sensitive to RNA secondary structure. In other preferred embodiments, an energetic profile of the polymerase processing the RNA template is generated that is a direct reflection of the nucleobase composition of the RNA template, e.g., where the dynamics of the polymerase are sensitive to the presence of certain types of nucleobases, e.g., modified or unnatural nucleobases. In particularly preferred embodiments, an energetic profile an a polymerase reflects both secondary structure and nucleobases composition of an RNA template being processed. For example, upon encountering secondary structure and/or unnatural or otherwise modified nucleotides in a template nucleic acid, the polymerase may exhibit pausing, an change in the incorporation duration, a change in the inter-pulse duration, and/or a change in the types of errors found in the resulting sequencing read, e.g., missed or extra pulses (sometimes termed "error metrics"). Further, such changes are often observed not only at the position of the secondary structure or modification, but also at positions flanking this position. Certain preferred methods for real-time monitoring of template-directed sequencing reactions (in particular those in which single molecules or molecular complexes are optically resolvable from one another and can be individually observed) to detect nucleic acid modifications (e.g., in the template) including secondary structure and base modifications (e.g., methylated bases) are provided in U.S. patent application Ser. No. 12/635,618, filed Dec. 10, 2009, and incorporated herein by reference in its entirety for all purposes. Further, the reaction conditions can be adjusted to modulate the sensitivity of the polymerase to RNA secondary structure and/or nucleobases composition, effectively making it more or less sensitive depending on the needs of the practioner. For example, the template can be pre-treated to introduce or alter modifications, e.g. to intensify the response of the polymerase at the position of interest. Alternatively or additionally, the temperature of an RNA sequencing reaction can be lowered to increase the stability of RNA secondary structure, and thereby increase the experimental sensitivity of the polymerase to the RNA secondary structure, or it can be raised to decrease the stability of the secondary structure at positions where the polymerase undergoes an overly long or permanent stall. Alternatively or additionally, agents known to affect the stability of secondary and/or tertiary structure of RNA (e.g., by modification of the thermal denaturation profiles of nucleic acids) can be included in a reaction mixture, and such agents are known to those of ordinary skill in the art and include, but are not limited to, betaine (e.g., glycine betaine), trimethylamine N-oxide (TMAO), polyols, diethylsulfoxide, dimethylsulfoxide, polyamines, methanol, urea, trehalose, proline, glycerol, low molecular weight amides (e.g., formamide, acetamide, pyrrolidone, etc.), pH, salt concentrations, divalent cation concentrations, etc. (See, e.g, Gluick, et al. (2003) J. Am. Chem. Soc. 125(15):4418-4419; Lambert, et al. (2007) J. Mol. Biol. 370(5):993-1005; Lee, et al. (1981) Proc. Natl. Acad. Sci. USA 78:2838-42; Chakrabarti, et al. (2001) Nuc. Ac. Res. 29(11):2377-81; Markarian, et al. (2006) Biopolymers 82(1):1-5; and Schwinefus, et al. (2007) Biochemistry 46(31):9068-9079, all of which are incorporated herein by reference in their entireties for all purposes.) Various types of modified nucleobases and nucleosides are known in the art, e.g., those provided in PCT Publication No. WO 2009/037473, and in Limbach, et al. (1994) Nuc. Ac. Res. 22(12):2183-2196, the disclosures of which are incorporated herein by reference in their entireties for all purposes.

Alternatively or additionally, the choice of nucleotide analog can affect the response of the polymerase to secondary structure and/or modified nucleosides in the template. The choice of labeling moiety and/or linker connecting the label to the nucleotide analog can cause an increased sensitivity of the polymerase to higher order structures in the template, e.g., resulting in longer pausing. For example, the incorporation of fluorescent nucleotides into DNA during PCR was described in Zhu, et al. (1997, Cytometry 28:206-211), which is incorporated herein by reference in its entirety for all purposes. Linkers for attaching a label to a biological molecule are well known in the art, and certain exemplary linkers are provided in U.S. Pat. No. 7,405,281; U.S. Patent Publication Nos. 20090233302, 20090325260, 20090246791, and 20090018324; and U.S. Ser. No. 12/621,352, filed Nov. 18, 2009, the disclosures of which are incorporated herein by reference in their entireties for all purposes.

Comparison of sequence reads for a given RNA template under various reaction conditions and/or in the presence of various agents can facilitate identification of regions of the RNA template that have such secondary structure. For example, the same RNA template can be sequenced in the presence and absence of a destabilizer of RNA secondary structure. The sequence reads generated comprise both nucleotide sequence data and kinetic data with regards to the rates of incorporation over the course of the reaction. The data generated in each reaction, and in particular the kinetics of nascent strand synthesis as the polymerase processes the template in each reaction, is combined and compared to identify regions of the RNA template that have secondary structure in the absence of the destabilizer based at least in part on the faster kinetics in the presence of the destabilizer. Further methods for detecting modifications in nucleic acid templates including secondary structure and bound agents are described in U.S. Ser. No. 12/635,618, filed Dec. 10, 2009, which is incorporated herein by reference in its entirety for all purposes.

Although the sequencing systems of the instant invention are capable of long readlengths, in certain embodiments it is preferred to cleave or fragment an RNA template prior to a template-dependent synthesis reaction. For example, where an RNA template is known to contain secondary and/or tertiary structure, cleavage of the template provides the ability to approach the higher-order structure from different positions on the template, or even from a portion of the template within such a structure in the complete, uncleaved molecule. Further, multiple copies of an RNA template of interest can be fragmented differently (e.g., by different enzymes or fragmentation conditions) to allow initiation at different locations on the template. As such, RNA template cleavage or fragmentation can be useful for facilitating differential secondary and/or tertiary structure processing by the polymerase, e.g., from different directions, in different sequence contexts, and under different conditions.

In certain embodiments, access to different portions of an RNA template can be achieved by using different primers complementary to different regions of the template. For example, a set of primers comprising primers specific to two or more regions of an RNA template can be used in primer extension reactions, e.g., with one or multiple primers present per reaction. For example, a single primer or plurality of primers is introduced to a reaction mixture comprising the RNA template and allowed to anneal to the template. The template-primer complexes are introduced to polymerases to form template-primer-polymerase complexes. A polymerase will bind a single template-primer complex at a single bound primer, and will commence primer extension to produce a nascent nucleic acid strand complementary to the template. If a plurality different primers and polymerases are present in the solution, then a subset of the polymerases will extend from each different primer. By monitoring nucleotide incorporations for each of the polymerases, reads from different regions of the template are generated. Methods of nucleic acid sequencing using multiple primers annealed in bulk and subsequent extension from only a single primer on a single template are further described in U.S. patent application Ser. No. 12/553,478, filed Sep. 3, 2009, which is incorporated herein by reference in its entirety for all purposes. In certain preferred embodiments, the sequence reads generated from different primers overlap, allowing comparison of sequence reads and enzyme kinetics in reactions having different locations of synthesis initiation. In some embodiments, primers bound to a template but not subject to primer extension serve to destabilize or disrupt secondary structure in the template, which can facilitate passage of the polymerase through the template and increase read length. In some embodiments, reactions are performed both in the presence and absence of multiple primers, and the resulting sequence reads are analyzed to determine if the presence of additional unextended primers annealed to the template affects the kinetics of the polymerase. Other agents that modify secondary structure can also be included in the reaction mixtures, as described elsewhere herein. In certain preferred embodiments, the template-primer-polymerase complexes are immobilized to be optically resolvable from one another, as described elsewhere herein.

In certain embodiments, the methods are used to perform intramolecular redundant sequencing, in which a template nucleic acid is used to generate multiple reads of a polynucleotide sequence present in the template, e.g., by virtue of multiple copies of the complement being present in the template, and/or by re-sequencing all or a portion of the template. Templates particularly suitable for repeated sequencing are circular nucleic acid molecules that can serve as templates for rolling circle replication. A template-primer-polymerase complex is formed and the polymerase extends the primer along the template sequence. After the polymerase has passed completely around the template, strand displacement can occur to displace the extended primer (primer and nascent strand) and the polymerase continues around the circular template. The product is a linear concatemer having the primer at the 5' end and multiple contiguous complementary copies of the template. Since the incorporation of nucleotides into this product is monitored, redundant sequence information is generated during synthesis of the multiple copies of the circular template. Using templates that allow repeated sequencing or resequencing of a single template increases the fold-coverage of the sequence reads for the template, thereby providing more data for further analysis, e.g., construction of sequence scaffolds and/or consensus sequences for the nucleic acid template. Further, the sequencing templates can optionally comprise additional sequences to facilitate various aspects of the analytical methods. For example, restriction sites can be incorporated for subsequent cleavage of the product and/or template. Additionally or alternatively, registration sequences can be included to permit the identification of certain regions of the template in the sequencing read, and such registration sequences provide a basis for aligning the sequence data from the redundant sequence reads and/or between sequences from separate but identical templates. Various methods for generating redundant sequence reads are known in the art, and certain methods useful with the methods described herein are provided in U.S. Pat. Nos. 7,302,146 and 7,476,503; U.S. Patent Publication Nos. 2009/0280538, 2009/0298075, and 2009/0029385; and U.S. Ser. No. 12/553, 478, filed Sep. 3, 2009, the disclosures of each of which are incorporated herein by reference in their entireties for all purposes. Further, methods for circularization of RNA molecules can be accomplished using ligase enzymes, such as T4 RNA ligase; more information on types and activities of various ligase enzymes is found in the art, e.g., in Pascal, J. M. (2008) Curr Op Structural Biology 18:96-105; Silber, et al. (1972) Proc. Nat. Acad. Sci. USA 69(10):3009-3013; El Omani, et al. (2006) J. Biol. Chem. 281:1573-9; Nandakumar, et al. (2006) Cell 127:71-84; and Ho, et al. (2004) Structure 12:327-339, the disclosures of which are incorporated herein by reference in their entireties for all purposes.

In some embodiments, template-switching activities of reverse transcriptase (RT) enzymes can be exploited for multiple rounds of RNA sequencing of one or more RNA templates. Briefly, RT has the ability to undergo intramolecular template-switching events by dissociating and reassociating with a template, which can result in deletions, insertions, and/or duplications in a nascent strand being generated. Further, intermolecular template-switching events can also occur, resulting in homologous or nonhomologous recombination. As such, the template-switching activity of RT plays an important role in generating variation in retroviral populations. In the context of the instant invention, template-switching by an immobilized RT can be used to sequence multiple different RNA templates at a single reaction site, even when those RNA templates are closed circles. Further, multiple different RNA templates can be immobilized at a particular reaction site, and an RT can switch from one to another, thereby sequencing multiple different templates at a single reaction site. Further information regarding the template switching activity of reverse transcriptase enzymes is available in the art, e.g., in Luo, et al. (1990) J Virol. 64(9): 4321-8; Mader, et al. (2001) J. Lab. Clinical Medicine 137 (6):422-8; and Bowman, et al. (1998) J. Virol. 72(6):5198-5206, the disclosures of which are incorporated herein by reference in their entireties for all purposes.

V. RNA-Dependent Polymerases

In accordance with the invention, improved performance of the overall system may be achieved through the identification and/or development of an efficient RNA-dependent polymerase sequencing "engine." Many reverse transcriptases, RNA-dependent RNA polymerases, or DNA polymerases with RNA-dependent polymerization activities, naturally exhibit features compatible with high-speed and long-readlength RNA sequencing (Table 1). Thus far, only two studies have investigated the incorporation of phospholinked nucleotides by reverse transcriptases (S. Kumar, et al., *Nucleos. Nucleot. Nucleic Acids* 2005, 24, 401; and B. A. Mulder, et al., *Nucleic Acids Res* 2005, 33, 4865, both of which are incorporated herein by reference in their entireties for all purposes), and both reports used DNA, not RNA, as templates. In both cases, despite very high phospholinked nucleotide concentrations (100 μM), measured polymerization speeds of HIV and AMV reverse transcriptases were ~100-fold lower compared to control experiments utilizing unmodified dNTPs. Further information on the following and other transcriptases and polymerases can be found in the art, e.g., in D. S. Gregerson, et al. (incorporated herein above); A. Bibillo, et al. (incorporated herein above); H. E. Huber, et al., *J Biol Chem* 1989, 264, 4669; B. Arezi, et al., *Nucleic Acids Res* 2009, 37, 473; O. Avidan, et al., *Eur J Biochem* 2002, 269, 859; M. Perach, et al., *Virology* 1999, 259, 176; R. Taube, et al., *Biochem J* 1998, 329 (Pt 3), 579; A. Kurzynska-Kokorniak, et al., *J Mol Biol* 2007, 374, 322; M. H. Lamers, et al., *Proc Natl Acad Sci USA* 2008, 105, 20565; L. Blanco, et al., *J. Biol. Chem.* 1989, 264, 8935; T. W. Myers, et al., *Biochemistry* 1991, 30, 7661; M. Ricchetti, et al., *EMBO J* 1993, 12(2):387-96; T. Kornberg, et al., in *The enzymes*, Vol. 10, 3rd ed. ed. (Ed.: B. P), Academic Press Inc., New York, 1974, pp. 119; R. A. Bambara, et al., *J Biol Chem* 1978, 253, 413; E. V. Makeyev, et al., *EMBO J* 2000, 19, 124; V. Lohmann, et al., *J Virol* 1997, 71, 8416; B. Mulder, et al., *Nuc. Ac. Res.* 2005, 33, 4865; Liu, et al., *FEBS Lett* 2006, 580(5):1497-1501; and P. Labonte, et al., *J Biol Chem* 2002, 277, 38838; as well as in various patents and patent applications, e.g., U.S. Patent Publication Nos. 20070196846, 20090176233, 20080108082; U.S. Ser. Nos. 12/384,112 and 12/384,110, both filed Mar. 30, 2008; U.S. Ser. No. 61/278,041, filed Sep. 30, 2009; U.S. Ser. No. 61/306,407, filed Feb. 19, 2010; and U.S. Ser. No. 12/584,481, filed Sep. 4, 2009, the disclosures of each of which are incorporated herein by reference in their entireties for all purposes.

TABLE 1

| | Processivity (bases) | Maximum speed (bases/s) | Strand-displacement DNA synthesis | Activity with phospholinked nucleotides | Need primer to initiate |
|---|---|---|---|---|---|
| Reverse Transcriptases | | | | | |
| Avian myeloblastosis virus (AMV)* | 1100 | 22 | limited (~50 bases) | limited | yes |
| Human immunodeficiency virus (HIV)* | 100 | 10-15 | limited (~50 bases) | limited | yes |
| Moloney Murine Leukemia Virus (M-MLV)* | 9000 | 1 | yes | unknown | yes |
| Bovine leukemia virus (BLV) | 60 | 4 | unknown | unknown | yes |
| Mouse mammary tumor virus (MMTV) | 550 | 11 | unknown | unknown | yes |
| Retrotransposon R2 | >600 | 30 | yes | unknown | yes |
| DNA polymerases with reverse transcriptase activity** | | | | | |
| *Geobacillus kaustophilus* | >50,000 (with β-clamp) | 700 | yes | unknown | yes |
| phi29 | >70,000 | 100 | yes | yes | yes |
| *Thermus thermophilus** | 300 | 120 | n.a. (thermophilic) | unknown | yes |
| *E. coli* pol I | ~50 | 17 | yes (degrades displaced strand) | unknown | yes |
| RNA-dependent RNA polymerases | | | | | |
| phi6 | 13,500 | 120 | yes | unknown | no |
| Hepatitis C NS5B | 20,000 | 3 | limited | unknown | yes |

*wild-type or published mutants;
**available values for DNA-dependent DNA polymerization In certain preferred embodiments, the RNA-dependent RNA polymerase phi6 is used in RNA sequencing reactions. This polymerase is highly processive, possesses strand-displacement activity, and is not generally blocked by secondary structure (e.g., hairpins, etc.) in a template RNA molecule. Further, it does not require a primer bound to the template to initiate synthesis, and can initiate at a 3' end of a template strand for "primer-independent synthesis" of a nascent strand. Further, it can synthesize using either a single-stranded or double-stranded RNA template. This enzyme is commercially available, e.g., from New England Biolabs®.

Development of improved RNA polymerases involves screening RNA-dependent polymerases against the large number of phospholinked dNTPs having varying structures in terms of fluorescent labels, linker groups, length of phosphate chains, and the like. For example, the fidelity of the enzyme can be affected by the chemical structure of the nucleotide analogs to which it binds. Effects of different fluorophores, linkers connecting the fluorophore and terminal phosphate, and the number of phosphates can thereby be determined. These screens can also be used to test RNA-dependent RNA polymerases, for which phospholinked ribonucleotides are synthesized. The chemical synthesis proceeds identically compared to deoxyribonucleotides (see, e.g., J. Korlach, et al., *Nucleos. Nucleot. Nucleic Acids* 2008, 27, 1072, which is incorporated herein by reference in its entirety for all purposes) with the starting nucleotide a ribonucleotide instead of a deoxyribonucleotide, and Alexa Fluor 647 aminohexyl G6P has been successfully synthesized to verify this hypothesis. Different reaction conditions can be screened to investigate the effect of temperature, ionic strength, pH, additives for altering RNA secondary structure stability (such as betaine, DMSO, etc.), and divalent catalytic metal ions ($Mg^{2+}$, $Mn^{2+}$, $Cr^{2+}$, $ca^{2+}$, etc.) concentrations on polymerization efficiencies.

Extensions on short (~40 bases) RNA templates are used for high temporal and spatial (e.g., base pair) resolution of incorporation efficiencies, while much longer (~1 kilobase) RNA templates are used to determine effects of template secondary structure. Generally, conventional primer extension assays and gel electrophoresis analysis may be used to monitor these processes. Measured parameters include speed ($k_{cat}$), affinity ($K_m$), processivity, strand-displacement activity, and mismatch incorporation. At the same time, phospholinked nucleotide incorporation assays are employed that are amenable to higher throughput used during the screening of enzyme mutant libraries (see below). These microtiter plate-based assays monitor bulk polymerization kinetics in real time, thereby providing quantitative values for polymerization efficiencies. Detected signals include, e.g., the binding of intercalating dyes to the newly formed duplex nucleic acid (see, e.g., M. Seville, et al., *Biotechniques* 1996, 21, 664, which is incorporated herein by reference in its entirety for all purposes), or the presence of inorganic phosphate by fluorescent probes such as the Phosphate Sensor™ (Invitrogen). For the latter assay, phospholinked nucleotide incorporation by polymerase yields a fluorophore-linker-(poly)phosphate reaction product that is a substrate for conversion to fluorophore-linker and inorganic phosphate in the presence of a phosphatase (see, e.g., J. Korlach, et al., *Nucleos. Nucleot. Nucleic Acids* 2008, 27, 1072, incorporated herein above).

As will be appreciated, improved polymerases may be prepared using molecular evolution programs and processes known in the art to improve their "sequence engine" performance. Such programs have been successfully exploited for the improvement of DNA polymerases for single molecule DNA sequencing processes and are expected to be analogously applicable to RNA-dependent polymerase candidates. For various in-silico methods and combinations of in-silico and in vitro methods, see, e.g., Schneider, et al. (1994) Comput Appl Biosci. 10(6):635-45; Wrede, et al. (1998) Biochemistry. 37(11):3588-93; Jonsson, et al. (1993) Nuc. Ac. Res. 21(3):733-739; Caffrey et al. (2007) BMC Bioinformatics 8:381; Gustafsson, et al. (2003) Curr. Opinion in Biotech. 14:366-370; Hellberg, et al. (1986) J. Medicinal Chemistry 30(7):1126-35; Jiang, et al. (2008) Science 319: 1387-91; Ashworth, et al. (2006) Nature. 441(7093):656-9; and Fox, et al. (2007) Nature Biotech. 25(3):338-44. Epub 2007 Feb. 18, the disclosures of all of which are incorporated herein by reference in their entireties for all purposes.

Diversification of the amino acid sequence space may be performed by mutagenic PCR and DNA shuffling, including, for example, the use of yeast displays for expression and selection (see, e.g., S. A. Gai, et al., *Curr Opin Struct Biol* 2007, 17, 467; and D. Lipovsek, et al., *Chem Biol* 2007, 14, 1176, both of which are incorporated herein by reference in their entireties for all purposes), in which ~$10^4$ copies of a recombinant protein are displayed on the surface of a single yeast cell carrying the transgene for the protein. The genotype-phenotype linkage is provided by the yeast cell, but no protein purification is necessary as the displayed proteins have the same properties as bulk solutions of polymerase. Selective pressures can be applied by the solution conditions, and biotin-tagged nucleotides or primers can be employed in incorporation-dependent template contexts for selection of desired polymerase activities over a large background. For example, selection pressure can be applied to the improved acceptance of phospholinked nucleotides, enhancing their affinities and thereby processivity of DNA synthesis.

Alternatively, in vitro molecular evolution is attractive for developing polymerases because the mutant protein can be screened for by challenging it to replicate its own gene, and several techniques of linking the expressed protein to their gene have been described (see, e.g., F. J. Ghadessy, et al., *Methods Mol Biol* 2007, 352, 237; H. Leemhuis, et al., *Curr Opin Struct Biol* 2005, 15, 472; and V. Stein, et al., *Chembiochem* 2007, 8, 2191, all of which are incorporated herein by reference in their entireties for all purposes). Advantages of in vitro evolution methods are their ability to enrich desirable mutants from very large libraries (~$10^9$) because the reactions are done in a single tube. Techniques such as compartmentalized self-replication, in which polymerases replicate their own genes in water-in-oil droplets, have already demonstrated the evolution of reverse transcriptases for novel or improved kinetic properties (see, e.g., F. J. Ghadessy, et al., *Proc Natl Acad Sci USA* 2001, 98, 4552; and J. L. Ong, et al., *J Mol Biol* 2006, 361, 537, both of which are incorporated herein by reference in their entireties for all purposes).

Rational engineering of these polymerases also may be employed by comparing the available high resolution crystal structures of RNA-dependent polymerases with other enzymes' crystal structures that have shown desirable properties for single-molecule DNA sequencing, and exploiting similar mutation strategies. For example, mutations in a polymerase can be introduced to modify its specificity for a given nucleotide or nucleotide analog. Further, it is well known that the activities, rates, and specificities of polymerases can be altered by varying the reaction conditions, e.g., by choice of divalent cation, pH, temperature, etc.

In an alternative aspect, the invention may operate through the capture/immobilization of the polymerase:template complex at the reaction site, e.g. in a ZMW, through the RNA template rather than the enzyme, as described previously. The template may be directly linked to the reaction site, or may be indirectly linked, e.g., through interaction with a primer or other moiety directly linked to the reaction site. Various types of template localization strategies are provided, e.g., in U.S. Ser. No. 12/562,690, filed Sep. 18, 2009; and U.S. Patent Publication No. 20050042633, both of which are incorporated by reference in their entireties for all purposes. Such a primer may be designed to be complementary to a particular region or multiple regions of interest in the RNA template(s), may be randomly generated, or may be an oligo(dT) that will anneal to the poly-dA tail on mRNAs. Loading of mRNA through hybridization to immobilized biotin-oligo(dT) is one preferred alternative approach, where the capture oligonucleotide simultaneously serves as the primer for enzyme binding and polymerization. For example, a universal biotin-oligo-dT primer captures all mRNA species in a sample through binding to the ubiquitous poly-A tail. RNA templates have previously been immobilized using this strategy, and various additional methods for immobilizing molecular complexes are provided, e.g., in U.S. Pat. No. 7,476,503, which is incorporated herein by reference in its entirety for all purposes. Selective capture of specific RNA templates preferably employs the use of sequence-specific primers, providing an in situ selection method. Detection and sequencing of very rare RNA templates over a large background of common RNA is thereby possible. The read lengths for RNA sequencing reactions in which the RNA template is immobilized are likely more limited that those for which the polymerase is immobilized because the site of polymerization may not always be within the observation volume. For example, in an embodiment in which the RNA template is immobilized by binding to an oligonucleotide on the substrate that also serves at the primer for initiation of synthesis, the site of polymerization is gradually pushed out of the ZMW detection volume as the polymerase translocates away from the initiation site. However, the reduced read lengths allow for the use of non-processive or less processive polymerases with this strategy.

VI. Detectable Labels

The present invention provides various methods for detection of components of various analytical reactions. In certain aspects, one or more components of an analytical reaction comprise detectable labels, e.g., that serve to signal a binding, incorporation, translocation, dissociation, or other catalytic event. Such labels can be detectable moieties known in the art including, but not limited to, chromophores (e.g., fluorophores and other dyes), quantum dots, non-fluorescent tags (e.g., surface enhanced Raman scattering (SERS) particles), scattering metallic nanoparticles (e.g., gold or silver), combinations of chromophores (e.g., FRET labels on a single or multiple components), intrinsic fluorescence, and the like. A variety of detectable labels have been developed in the art, including those described in U.S. Pat. Nos. 6,399,335, 5,866, 366, 7,476,503, and 4,981,977; U.S. Patent Pub. No. 2003/0124576; U.S. Ser. No. 61/164,567; WO 01/16375; Mujumdar, et al Bioconjugate Chem. 4(2):105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(11):2803-2812, 1992; and Mujumdar, et al, Bioconjugate Chem. 7:356-362, 1996; Intrinsic Fluorescence of Proteins, vol. 6, publisher: Springer US, ©2001; Kronman, M. J. and Holmes, L. G. (2008) Photochem and Photobio 14(2): 113-134; Yanushevich, Y. G., et al. (2003) Russian J. Bioorganic Chem 29(4) 325-329; and Ray, K., et al. (2008) J. Phys. Chem. C 112(46): 17957-17963, all of which are incorporated herein by reference in their entireties for all purposes. Many such labeling groups are commercially available, e.g., from the Amersham Biosciences division of GE Healthcare, and Molecular Probes/Invitrogen Inc. (Carlsbad, Calif.), and are described in 'The Handbook—A Guide to Fluorescent Probes and Labeling Technologies, Tenth Edition' (2005) (available from Invitrogen, Inc./Molecular Probes and incorporated herein in its entirety for all purposes). Further, a combination of the labeling strategies described herein and known in the art for labeling reaction components can be used.

In certain embodiments, detectable labels undergo Förster resonance energy transfer (FRET), and such labels are termed "FRET labels" herein. FRET labels typically comprise at least two chromophores that engage in FRET such that at least a portion of the energy absorbed by at least one "donor chromophore" is transferred to at least one "acceptor chromophore," which emits at least a portion of the transferred energy as a detectable signal contributing to an emission spectrum. In some embodiments, the donor and acceptor reside on a single molecule that undergoes a conformational change that affects the emitted signal, e.g., by varying the distance between them. Alternatively, the donor and acceptor can reside on different molecules that, during the course of a reaction (e.g., during incorporation of an amino acid), bring the chromophores near enough to each other to undergo FRET. Any of a number of fluorophore combinations can be selected for use in the present invention (see for example, Pesce et al., eds, Fluorescence Spectroscopy, Marcel Dekker, New York, 1971; White et al., Fluorescence Analysis: A practical Approach, Marcel Dekker, New York, 1970; Handbook of Fluorescent Probes and Research Chemicals, 6th Ed, Molecular Probes, Inc., Eugene, Oreg., 1996; all of which are incorporated herein by reference in their entireties for all purposes). In general, a preferred donor fluorophore is selected that has a substantial spectral overlap with the acceptor fluorophore. Additional examples of useful FRET labels include, e.g., those described in U.S. Pat. Nos. 5,654,419, 5,688,648, 5,853,992, 5,863,727, 5,945,526, 6,008,373, 6,150,107, 6,177,249, 6,335,440, 6,348, 596, 6,479,303, 6,545,164, 6,849,745, 6,696,255, and 6,908,769; Published U.S. Patent Application Nos. 2002/0168641, 2003/0143594, and 2004/0076979; and U.S. Ser. No. 61/164,567, filed Mar. 30, 2009, the disclosures of which are incorporated herein by reference for all purposes. Further, Förster-type resonant energy transfer can also be influenced by metal nanoparticles (see, e.g., Reil, F., et al. (2008) Nano Lett. 8(12); 4128-4133, incorporated herein by reference in its entirety for all purposes).

In certain embodiments, detectable labels are semiconductor nanocrystals such as quantum dots. Quantum dots are particularly significant for optical applications due to their theoretically high quantum yield. High-quality quantum dots are well suited for optical encoding and multiplexing applications due to their broad excitation profiles and narrow/symmetric emission spectra. Quantum dots have been found to have certain beneficial characteristics, including high brightness (owing to the high quantum yield) and high photostability, allowing real-time tracking of molecules and cells over extended periods of time (see, e.g., M. Dahan, et al. (2003) "Diffusion dynamics of glycine receptors revealed by single-quantum dot tracking," Science, vol. 302, pp. 442-445). Quantum dots are known in the art and include those described in U.S. Pat. Nos. 6,207,392, 6,114,038, 6,326,144, 7,192,785, 7,405,434, 7,460,960; Chan et al. (1998) "Quantum Dot Bioconjugates for Ultrasensitive Nonisotopic Detection" Science 281:2016-2018; Bruchez et al. (1998) Science 281:2013-2016. Quantum dots are commercially available from Invitrogen Corporation (Carlsbad, Calif.). Additional information on preparation, characteristics, and methods for using of various quantum dots can be found in the art, e.g. in Bawendi et al. (1993) J. Am. Chem. Soc. 115:8706; Dabbousi et al. (1997) J. Phys. Chem. B 101:9463; Danek et al. (1996) Chem. Mater. 8:173-179; Effros et al. (1996) Physical Review B. 54:4843-4856; Empedocles et al. (1996) Physical Review Letters 77:3873-3876; Goldman et al. (2002) J. Am. Chem. Soc. 124:6378-82; Murakoshi et al. (1998) J. Colloid Interface Sci. 203:225-228; Murray et al. (1993) J. Am. Chem. Soc. 115:8706-8714; Murray et al. (1996) Science 270: 1355-1338; Nirmal et al. (1996) Nature 383:802-804; Norris et al. (1996) Physical Review B. 53:16338-16346; Pathak et al. (2001) J. Am. Chem. Soc. 123:4103-4; Peng et al. (1997) J. Am. Chem. Soc. 119:7019-7029; Remade et al. (2000) Proc. Natl. Sci. USA 18:553-8; Rodriguez-Viejo et al. (1997) Appl. Phys. Lett. 70:2132-2134; Sacra et al. (1996) J. Chem. Phys. 103:5236-5245; and Optical Materials and Engineering News (1995) Vol. 5, No. 12, the disclosures of which are incorporated herein by reference in their entireties for all purposes.

In certain embodiments, detectable labels are surface enhanced Raman scattering (SERS) particles. Surface enhanced Raman spectroscopy or surface enhanced Raman scattering, often abbreviated SERS, is a technique that involves the enhancement of Raman scattering by molecules absorbed on a metal surface. The enhancement factor can be as much as 1014-1015, which allows the technique to be sensitive enough to detect single molecules. The use of SERS particles may be particularly beneficial in certain embodiments since at least ten or more types are commercially available (e.g., from Nanopartz (Salt Lake City, Utah), Oxonica (Mountain View, Calif.), and Nanospectra Biosciences (Houston, Tex.)) that have unique spectral emission signatures, thereby allowing great flexibility in differential labeling of multiple components of a reaction mixture. Further, SERS particles also have a high photostability, so are less susceptible to photobleaching or photo-induced damage than certain other detectable labels. Additional information on preparation, characteristics, and methods for using of various SERS particles can be found in the art, e.g. in U.S. Pat. Nos. 7,515,269, 7,511,808, and 7,485,471; PCT Publication Nos. WO/2003/095973 and WO/2008/001978; Nie, S. and Emory, S. R. (1997) Science 275 (5303): 1102-1106; Petrov, D. V. (2007) J. Opt. A: Pure Appl. Opt. 9 S139-S156; Culha, M. et al. (2003) Expert Rev Mol Diagn 3(5): 669-75; Culha, M. et al. (2003) Anal Chem 75(22): 6196-201; and Boncheva, M., et al. (1999) Langmuir 15: 4317, all of which are incorporated herein by reference in their entireties for all purposes.

In further embodiments, combinations of different kinds of labeling groups can be used on different reaction components in a single analytical reaction mixture. For example, chromophore-based labels (e.g., fluorescent dyes) can be linked to a subset of reaction components while SERS labels or quantum dots are linked to a different subset of reaction components. Further, multi-component labels may comprise a combination of different types of labeling groups; for example, a FRET pair can comprise a quantum dot donor and a fluorophore acceptor. The combinations of types of labels used and which reaction components are labeled need only ensure optical distinguishability between reaction components in order to provide the desired reaction characteristic(s) (e.g., sequence of nucleotides incorporated or kinetic characteristics such as rate, processivity, fidelity, etc.) desired by the investigator.

Detectable labels for use with the compositions, methods, and systems described herein can be attached to various and multiple components of an analytical reaction mixture. For example, one or more may be attached to a polymerase, nucleotide, template, damage-binding agent, component of the damage repair machinery, or a combination thereof. Preferred labels are those that do not substantially impede the continuous and processive nature of an analytical reaction of interest. Methods for detection and analysis of signals emitted from detectable labels are known in the art and certain preferred methods are further described in, e.g., U.S. Pat. Nos. 7,297,532 and 7,329,492; U.S. Patent Publication Nos. 20090024331, 20060228708, 20070036511, 20080080059, 20070188750, 20080277595, and 20070206187; Korlach, et al. (2008) Nucleosides, Nucleotides and Nucleic Acids 27:1072-1083; Eid, et al. (2009) Science 323:133-138; Blanchard (2004) PNAS 101(35):12893-12898; Lundquist, et al. (2008) Optics Letters 33(9):1026-1028; Wang, et al. (2007) Biochemistry 46:10767-10775; Uemura et al. (2008) Nucleic Ac. Res. 36(12):e70; Miyake et al. (2008) Anal. Chem. 80:6018-6022; and Levene, et al. (2003) Science 299:682-686, all of which are incorporated herein by reference for all purposes.

Further, the use of a label that is not constantly present at the reaction site is beneficial in various ways, including mitigation of photo-induced damage that could otherwise negatively impact the ongoing reaction. The term "photo-induced damage" generally refers to any direct or indirect impact of illumination, directed or emitted, on one or more reagents in a reaction resulting in a negative impact upon that reaction. For example, the long-lived triplet-state species of many fluorescent dye molecules exhibits a high degree of chemical reactivity that often results in photobleaching and the production of damaging free radicals and reactive intermediates. For a labeled reaction component that is constantly exchanged during the course of the reaction, e.g., nucleotide that loses its label upon incorporation into a nascent polynucleotide, the problems associated with photobleaching of a stationary label (e.g., one linked to an immobilized polymerase that is continually in the reaction site) would be mitigated. Further, the risk of photo-induced damage to other reaction components that can be immobilized in the reaction site is reduced since the potentially damaging emissions of signal from the label are not constant; that is, such emissions are limited to those periods of time during which the label is present in the reaction site, e.g., during binding until incorporation. Other methods for mitigating photo-induced damage and/or other methods for illuminating an analytical reaction (e.g., intermittent illumination) that may be combined with the methods, compositions, and systems of the invention are provided, e.g., in U.S. Ser. No. 61/116,048 (filed Nov. 19, 2008), Ser. No. 12/622,375 (filed Nov. 19, 2009), 61/139,402 (filed Dec. 19, 2008), Ser. No. 12/413,226 (filed Mar. 27, 2009), Ser. No. 12/561,221 (filed Sep. 16, 2009), and 61/127,435 (filed May 13, 2008); and in U.S. Patent Pub. Nos. 20070128133, 20090325260, and 20100003765, the disclosures of all of which are incorporated herein by reference in their entireties for all purposes.

VII. Optical Confinements

In certain aspects, the methods provide a means for studying analytical reactions in vitro by immobilizing at least one component of a analytical reaction in an optical confinement, labeling at least one other component, and detecting signals from the optical confinement during the reaction in real time. An optical confinement is preferentially configured to provide tight optical confinement so only a small volume of the reaction mixture is observable, i.e., signals can only be detected from a small volume of the reaction mixture. In certain embodiments, optical confinement technologies include zero mode waveguides, total internal reflection microscopy (TIRF), and/or optical waveguides (planar or otherwise configured). For example, in embodiments in which excitation illumination is used to excite chromophore-containing labels, the tight optical confinement allows only a small volume of the reaction mixture to be illuminated, and therefore limits excitation to only those chromophores within that small volume. As such, only the chromophores present in the small illuminated volume are excited and emit signals that are detectable by the optical system. This feature of the invention is useful for reducing the background signal from freely diffusing detectably labeled components in the reaction mixture, thereby enabling the use of physiological concentrations of these reagents. Some such optical confinements and methods of manufacture and use thereof are described at length in, e.g., U.S. Pat. Nos. 7,302,146. 7,476,503, 7,313,308, 7,315,019, 7,170,050, 6,917,726, 7,013,054, 7,181,122, and 7,292,742; U.S. Patent Publication Nos. 20080128627, 20080152281, and 200801552280; and U.S. Ser. No. 11/981,740, all of which are incorporated herein by reference in their entireties for all purposes.

Providing such individually resolvable configurations can be accomplished through a number of mechanisms, and typically involves immobilization of at least one component of an analytical reaction at a reaction site. For example, by providing a dilute solution of complexes on a substrate surface suited for immobilization, one will be able to provide individually optically resolvable complexes. (See, e.g., European Patent No. 1105529 to Balasubramanian, et al., the full disclosure of which is incorporated herein by reference in its entirety for all purposes.) Alternatively, one may provide a low density activated surface to which complexes are coupled. (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation. In preferred embodiments, a substrate comprises at least one optical confinement in which a molecule or molecular complex is immobilized and monitored. The optical confinement is a structure configured to isolate the immobilized molecule/complex from any other molecule/complex immobilized on the substrate, and in particular to isolate any detectable signals emitted from the optical confinement from any other signals emitted from any other optical confinements on the substrate. Such isolation allows the practitioner of the instant invention to unambiguously assign a detected signal to a single optical confinement on the substrate, and therefore to a single analytical reaction on the substrate.

The immobilization of a component of an analytical reaction can be engineered in various ways. For example, an enzyme (e.g., polymerase, transcriptase, kinase, etc.) may be attached to the substrate at a reaction site. In other embodiments, a substrate in an analytical reaction (for example, a nucleic acid template, e.g., DNA, RNA, or hybrids, analogs, and mimetics thereof, or a target molecule for a kinase) may be attached to the substrate at a reaction site. One skilled in the art will appreciate that there are many ways of immobilizing nucleic acids and proteins into an optical confinement, whether covalently or non-covalently, via a linker moiety, or tethering them to an immobilized moiety. These methods are well known in the field of solid phase synthesis and microarrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art. In some embodiments, a nucleic acid template is immobilized onto a reaction site (e.g., within an optical confinement) by attaching a primer comprising a complementary region at the reaction site that is capable of hybridizing with the template, thereby immobilizing it in a position suitable for monitoring. In certain embodiments, an enzyme complex is assembled in an optical confinement, e.g., by first immobilizing an enzyme component. In other embodiments, an enzyme complex is assembled in solution prior to immobilization. Additional methods for immobilization are provided in U.S. Ser. Nos. 11/645,125 and 11/645,135, both of which were filed Dec. 21, 2006; and U.S. Patent Publication No. 20080199932, all of which are incorporated herein by reference in their entireties for all purposes.

Where desired, an enzyme or other protein reaction component to be immobilized may be modified to contain one or more epitopes such as Myc, HA (derived from influenza virus hemagglutinin), poly-histadines, and/or FLAG, for which specific antibodies are available commercially. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention.

The binding moieties or agents of the reaction components they immobilize can be applied to the support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

In some embodiments, a substrate comprising an array of reaction sites is used to monitor multiple biological reactions, each taking place at a single one of the reaction sites. Various means of loading multiple biological reactions onto an arrayed substrate are known to those of ordinary skill in the art and are described further, e.g., in U.S. Ser. No. 61/072,641, incorporated herein by reference in its entirety for all purposes. For example, basic approaches include: creating a single binding site for a reaction component at the reaction site; removing excess binding sites at the reaction site via catalytic or secondary binding methods; adjusting the size or charge of the reaction component to be immobilized; packaging or binding the reaction component within (or on) a particle (e.g., within a viral capsid), where a single such particle fits into the relevant reaction site (due to size or charge of the particle and/or observation volume); using non-diffusion limited loading; controllably loading the reaction component (e.g., using microfluidic or optical or electrical control); sizing or selecting charges in the reaction sites/observation volumes (e.g., the sizes of optical confinements in an array) to control which reaction components will fit (spatially or electrostatically) into which reaction sites/observation volumes; iterative loading of reaction components, e.g., by masking active sites between loading cycles; enriching the activity of the reaction components that are loaded; using self-assembling nucleic acids to sterically control loading; adjusting the size of the reaction site/observation volume; and many others. Such methods and compositions provide for the possibility of completely loading single-molecule array reaction sites (instead of about 30% of such sites as occurs in "Poisson limited" loading methods) with single reaction components (e.g., molecular complexes).

The optical confinements can be further tailored in various ways for optimal confinement of an analytical reaction of interest. In particular, the size, shape, and composition of the optical confinement can be specifically designed for containment of a given enzyme complex and for the particular label and illumination scheme used.

VIII. Systems

The invention also provides systems that are used in conjunction with the compositions and methods of the invention in order to provide for real-time single-molecule detection of analytical reactions. In particular, such systems typically include the reagent systems described herein, in conjunction with an analytical system, e.g., for detecting data from those reagent systems. In certain preferred embodiments, analytical reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously (e.g., multiple types of differentially labeled reaction components). A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, the invention provides data processing systems for transforming raw data generated in an analytical reaction into analytical data that provides a measure of one or more aspects of the reaction under investigation, e.g., transforming signals from a sequencing-by-synthesis reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Patent Publication No. 20090024331 and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data; c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed, a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

Figure 3:
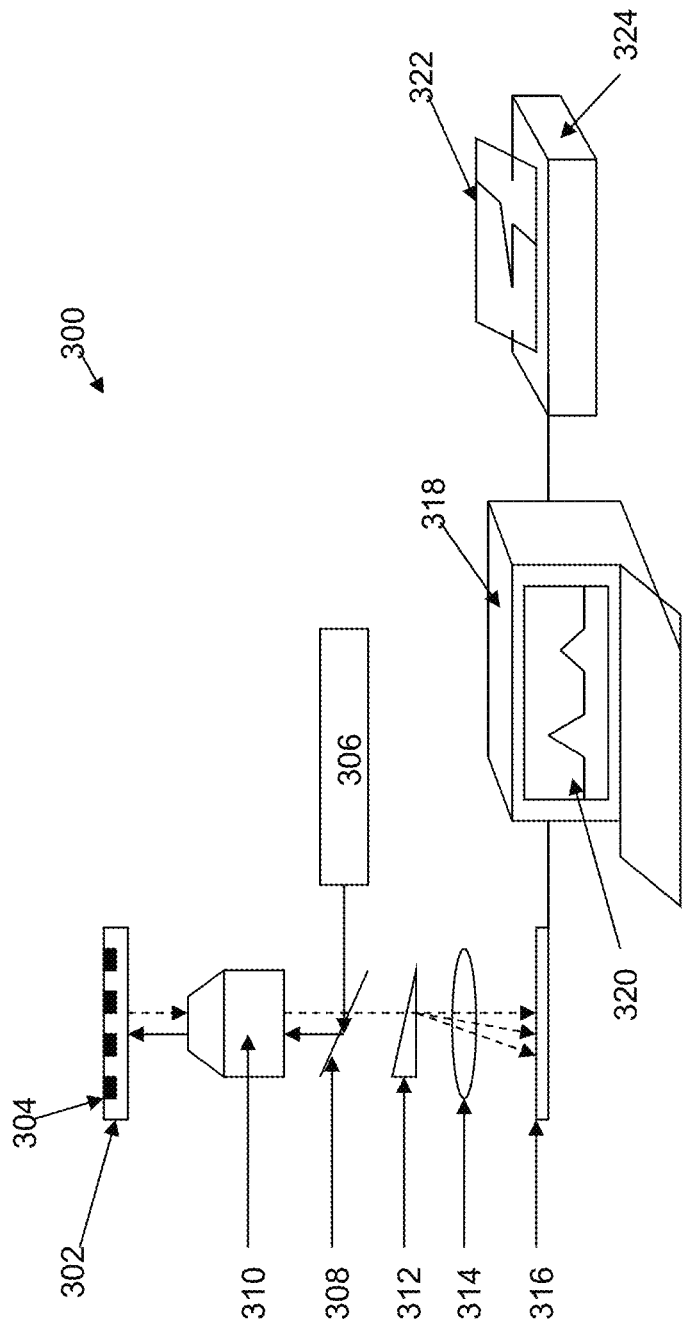
FIG. 3 schematically illustrates one embodiment of a system for use with the methods, devices, and systems of the invention.

As shown in FIG. 3, the system 300 includes a substrate 302 that includes a plurality of discrete sources of chromophore emission signals, e.g., an array of zero mode waveguides 304. An excitation illumination source, e.g., laser 306, is provided in the system and is positioned to direct excitation radiation at the various signal sources. This is typically done by directing excitation radiation at or through appropriate optical components, e.g., dichroic 308 and objective lens 310, that direct the excitation radiation at the substrate 302, and particularly the signal sources 304. Emitted signals from the sources 304 are then collected by the optical components, e.g., objective 310, and passed through additional optical elements, e.g., dichroic 308, prism 312 and lens 314, until they are directed to and impinge upon an optical detection system, e.g., detector array 316. The signals are then detected by detector array 316, and the data from that detection is transmitted to an appropriate data processing system, e.g., computer 318, where the data is subjected to interpretation, analysis, and ultimately presented in a user ready format, e.g., on display 320, or printout 322, from printer 324. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901, 273, all of which are incorporated herein by reference in their entireties for all purposes.)

IX. Examples

Efficient synthesis of a complementary DNA strand using an RNA-dependent DNA polymerase with complete replacement of unmodified dNTPs with phospholinked nucleotides carrying four distinct fluorescent labels was compatible with a single-molecule, real-time detection platform (Pacific Biosciences of California, Menlo Park, Calif.). Detection of incorporation of phospholinked nucleotides by single reverse transcriptase molecules immobilized in ZMWs were performed using synthetic RNA templates and four differentially-labeled nucleotide analogs.

Figure 4A:
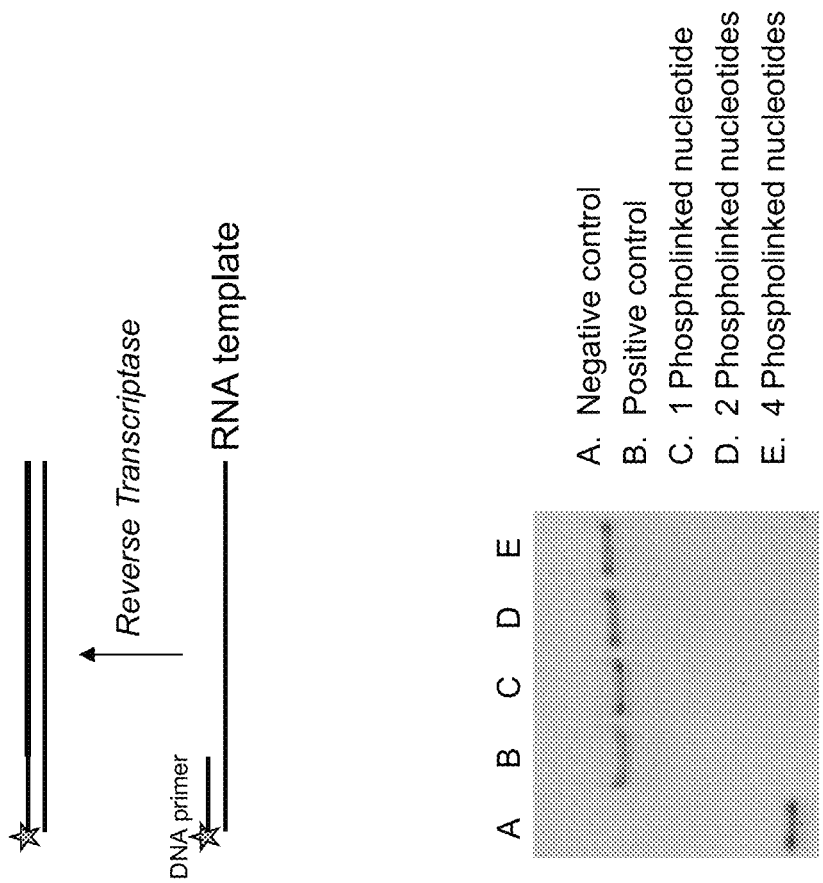

FIG. 4 provides results showing bulk and single-molecule incorporation of phospholinked dNTPs by a mutant reverse transcriptase. For the bulk assay (FIG. 4A), the synthetic, linear RNA template (36 bases) contained a 5'-FAM-labeled DNA primer (16 bases), allowing for 20 dNTP incorporations during reverse transcriptase-mediated cDNA synthesis. Reverse transcriptase enzyme (100 nM) was bound to primed RNA template (100 nM) for 5 minutes at 37 degrees Celsius in a buffer containing 50 mM Tris-HCl, pH 8.0, 10 mM KCl, 0.1 mM CaCl$_2$, and 5 mM DTT (buffer A), and 1 micromolar of phospholinked nucleotide (Alexa Fluor 555 dT6P) complementary to the first base in the RNA template, then placed on ice. Thereafter, 0.1 mM EGTA and 5 mM MgCl$_2$ as well as the other 3 phospholinked or unmodified nucleotides were added (at 1 micromolar each), the reactions were incubated for 5 minutes at 37 degrees Celsius, then run on a 0.8% agarose gel, and imaged with a typhoon imager (Applied Biosystems). The gel illustrated in FIG. 4A has the following lane assignments: A. unmodified dNTPs, −dTTP (negative control; dTTP is the first base to be incorporated); B. unmodified dNTPs (positive control); C. one phospholinked dNTP replacing one unmodified dNTP; D. two phospholinked dNTPs replacing two unmodified dNTPs; E. all four unmodified dNTPs are replaced by four distinctly labeled phospholinked dNTPs.

For the single-molecule assays (FIG. 4B), the synthetic, linear RNA template (36 bases) contained a 5'-biotin-labeled DNA primer (16 bases), allowing for 20 dNTP incorporations during reverse transcriptase-mediated cDNA synthesis. Reverse transcriptase enzyme (100 nM) was bound to primed RNA template (100 nM) for 5 minutes at 37 degrees Celsius in a buffer containing 50 mM Tris-HCl, pH 8.0, 10 mM KCl, 0.1 mM CaCl$_2$, and 5 mM DTT (buffer A), and 1 micromolar of phospholinked nucleotide (Alexa Fluor 555 dT6P) complementary to the first base in the RNA template, then placed on ice. The complex was diluted to 4 nM final concentration in buffer A, additionally containing 2 mM PCA, 5 uM PCD, 5 mM Trolox, and 2 mM FMP (buffer B), and the other three phospholinked nucleotides at 1 micromolar. ZMW arrays were wetted with 40 microliters of buffer A, the solution was discarded, and then the chips were incubated with 25 μl of the diluted reaction solution for 1 minute at 37 degrees Celsius before placing into the instrument. The sequencing was initiated by robotic addition of 10 μl of buffer B, additionally containing 0.1 mM EGTA and 5 mM MgCl$_2$.

FIG. 4B shows a representative time trace of fluorescence intensity from an individual ZMW. These results demonstrate that the methods described herein are capable of single-molecule, real-time RNA sequencing. The trace demonstrates that the ternary complex was successfully loaded into ZMW arrays, the polymerization reaction was initiated, and successive phospholinked nucleotide incorporations by the reverse transcriptase were successfully detected at the single molecule level, using tailored synthetic RNA templates. The formation of the ternary complex consisting of reverse transcriptase, primed RNA template, and cognate phospholinked nucleotide was also independently demonstrated, in bulk solution, as measured by fluorescence correlation spectroscopy (data not shown).

Figure 5A:
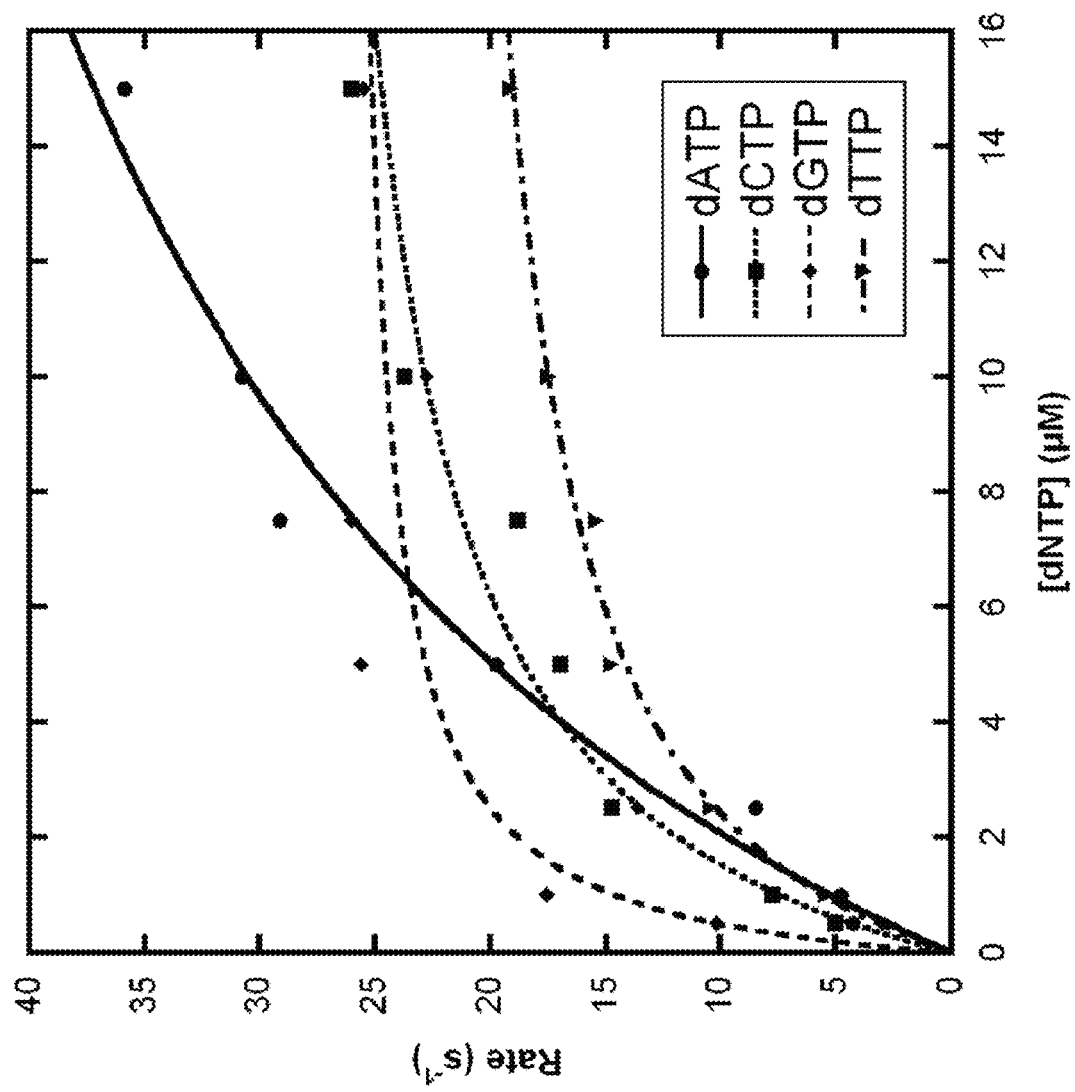
Figure 5B:
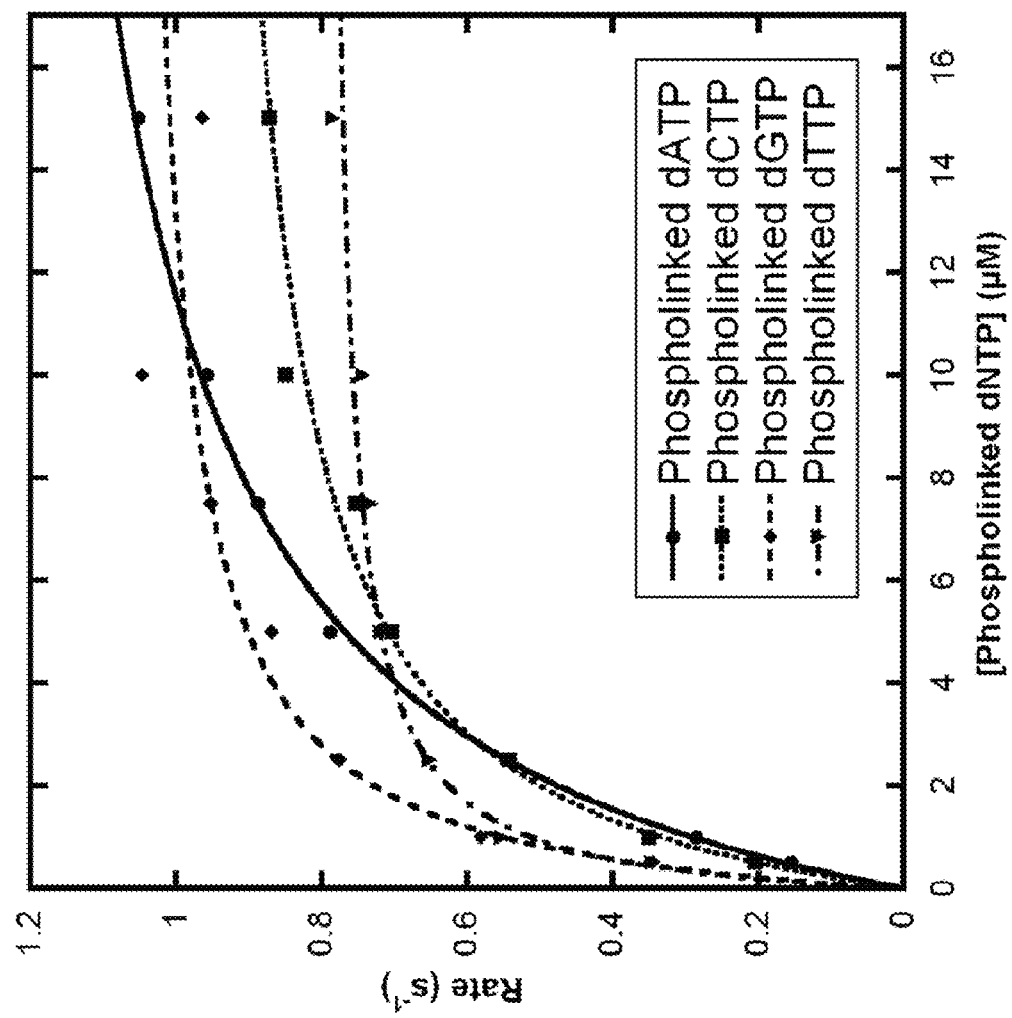

The kinetic properties of cDNA synthesis using 100% labeled nucleotides were similar compared to synthesis using unmodified nucleotides. Quenched-flow experiments were carried out on a quenched flow instrument (KinTek Corporation, USA), at 37 degrees Celsius using a water bath. The quenched flow time was 50 ms. A concentration series of different nucleotide concentrations was performed as follows: Syringe 1 contained reverse transcriptase enzyme (400 nM) and DNA template (200 nM) in a buffer containing 50 mM Tris-acetate, pH 7.84 at room temperature (pH 7.5 at 37 degrees Celsius), 100 mM Potassium acetate, and 0.1 mM EDTA, in a total volume of 200 microliters, and was used for multiple injections. Syringe 2 contained the same buffer, additionally including 12.5 mM magnesium acetate, and nucleotides at various concentrations, ranging from 0.25 to 15 micromolar, at a volume of 20 microliters for each concentration for single injections. Samples were analyzed by capillary electrophoresis using a 3730XL instrument (Applied Biosystems). FIG. 5 contains two plots illustrating the rate of nucleotide incorporation by the polymerase. Plot A provides the results in the presence of unmodified nucleotides; and plot B provides the results in the presence of phospholinked nucleotide analogs. Table C lists the $K_{cat}$ (s$^{-1}$) and $K_m$ (μM) for each of the four unmodified nucleotides and each of the four phospholinked nucleotide analogs.

Figure 6B:
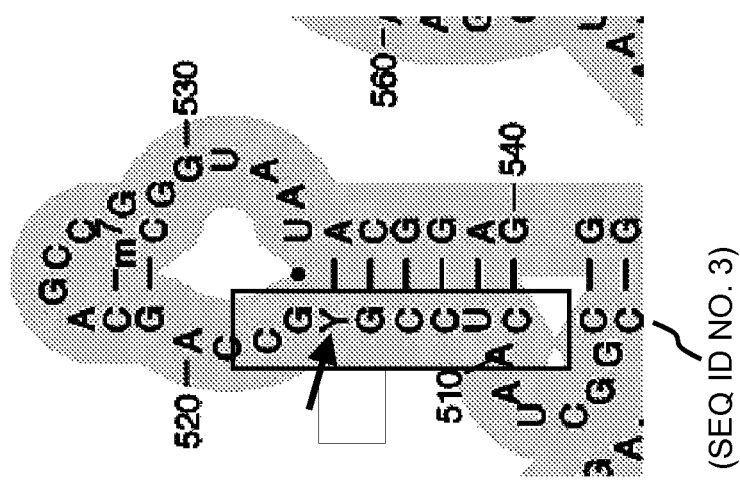
FIG. 6A-6F provides results from template-dependent synthesis reactions using a reverse transcriptase and a template having a pseudouridine residue. The molecular structure of pseudouridine (A) and the location of the residue in the template (B) are provided. Plots are provided showing an extended incorporation duration in the vicinity of pseudouridine (C & D).
Figure 6A:
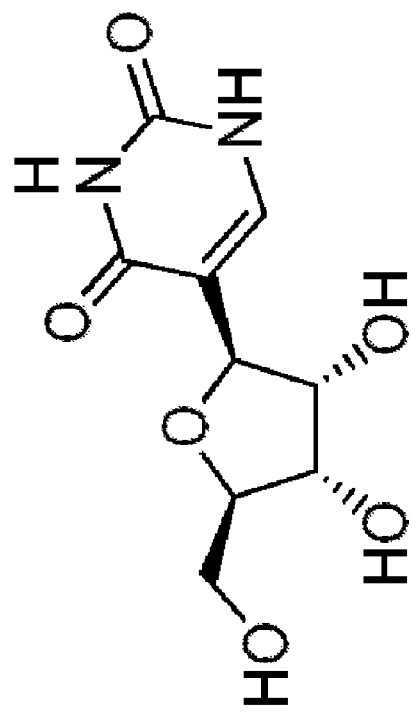
Figure 6C:
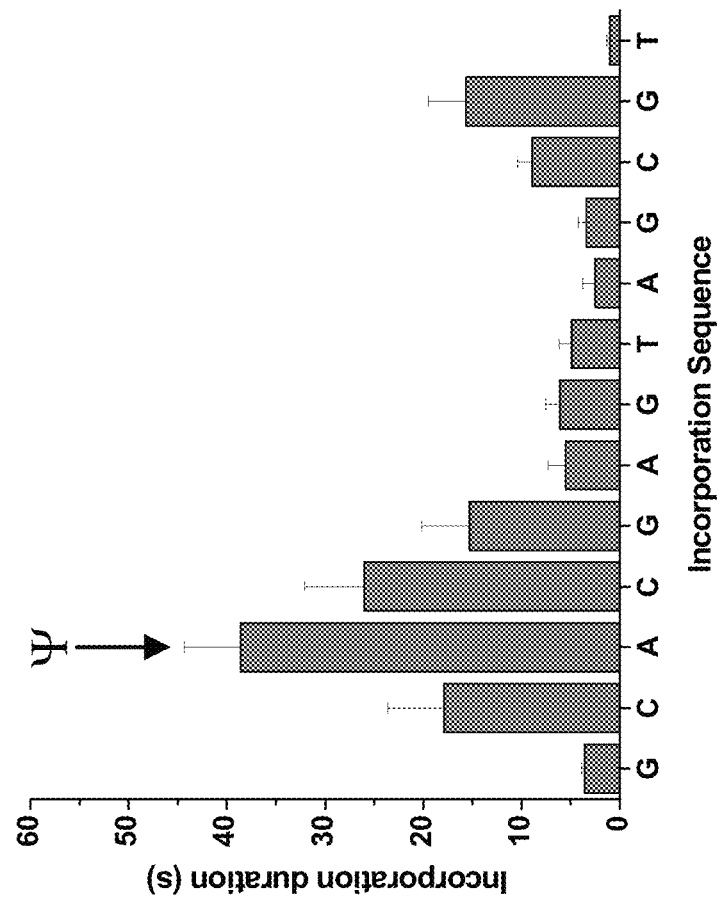
Figure 6D:
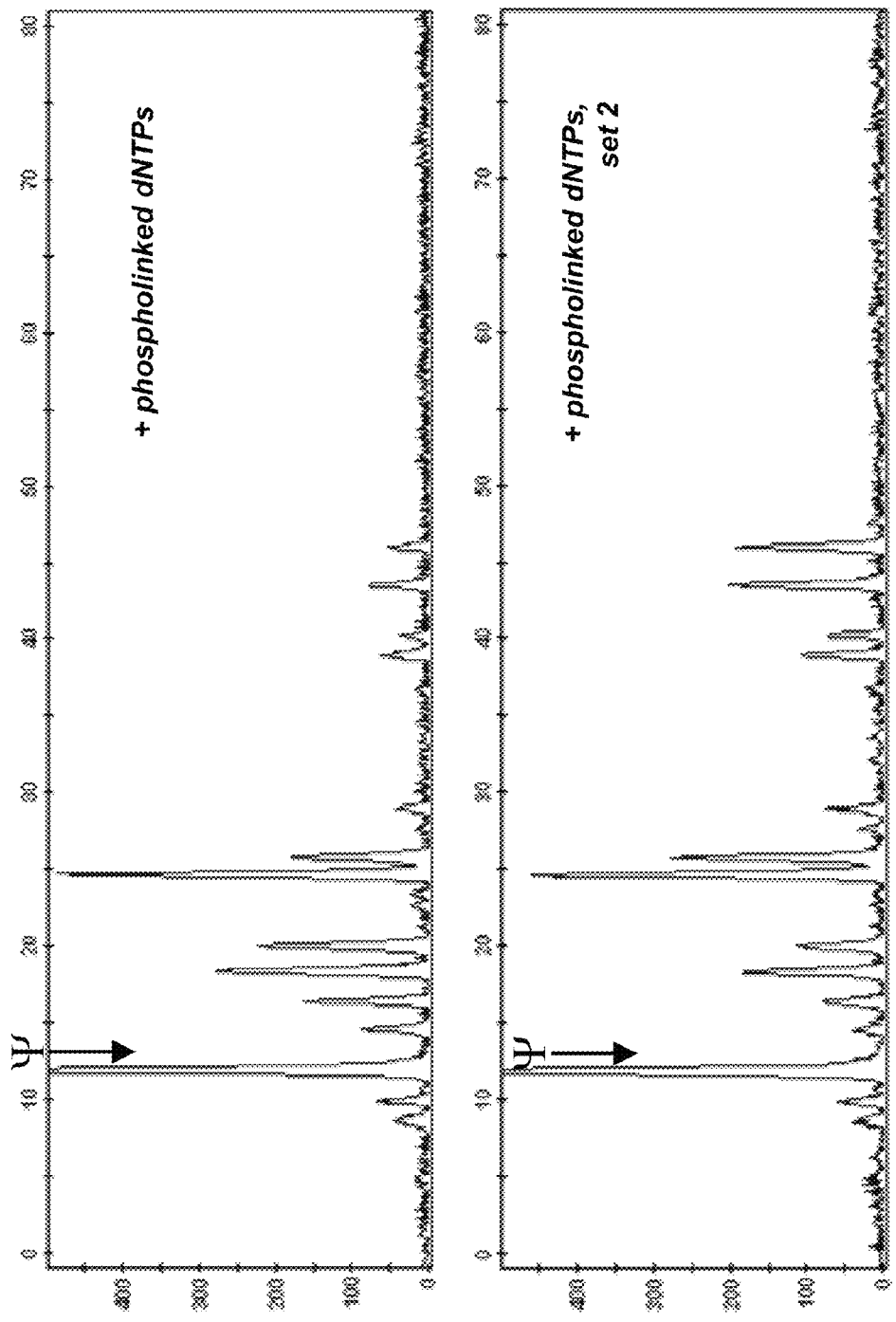
Figure 6E:
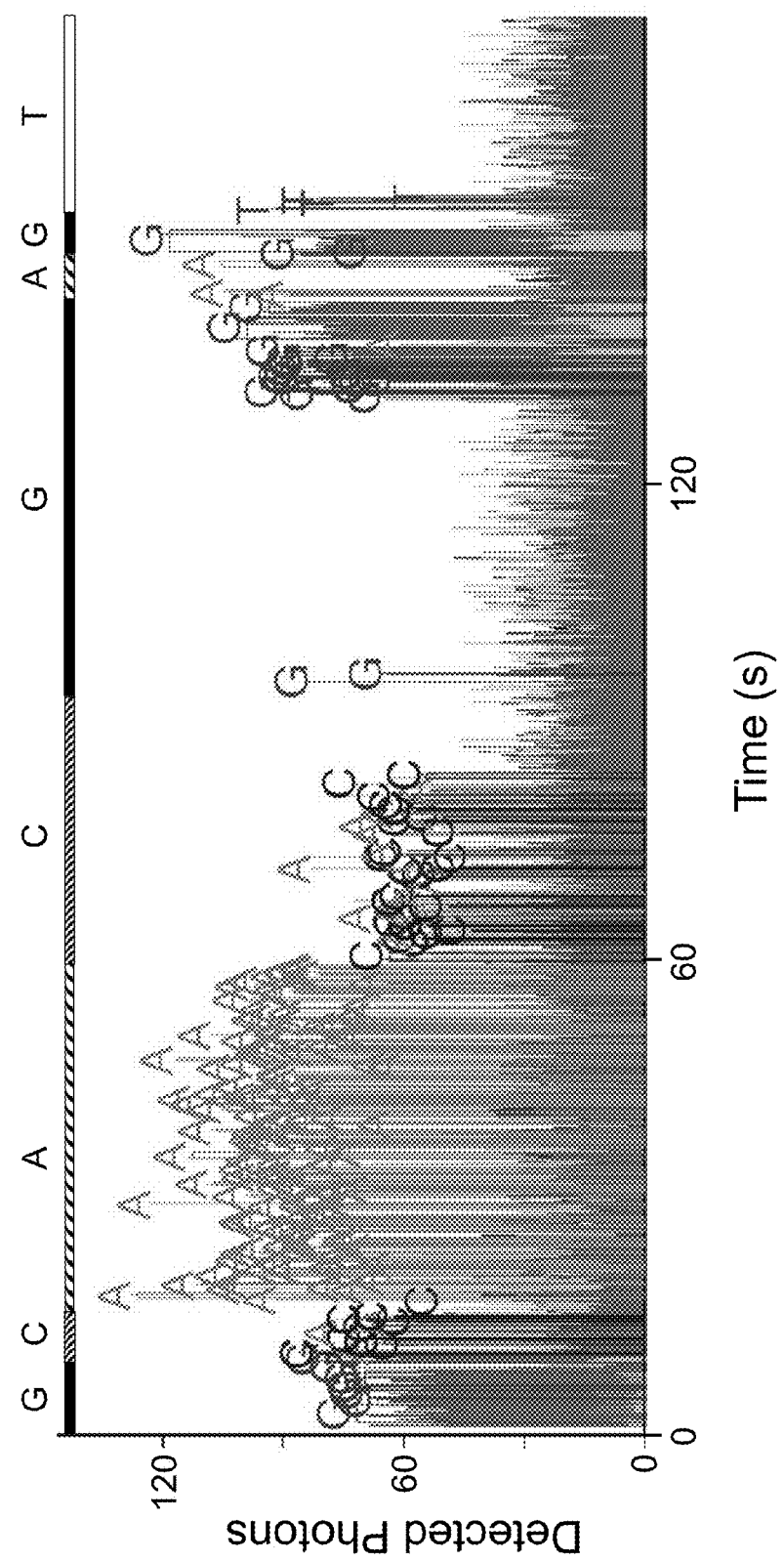
Figure 6F:
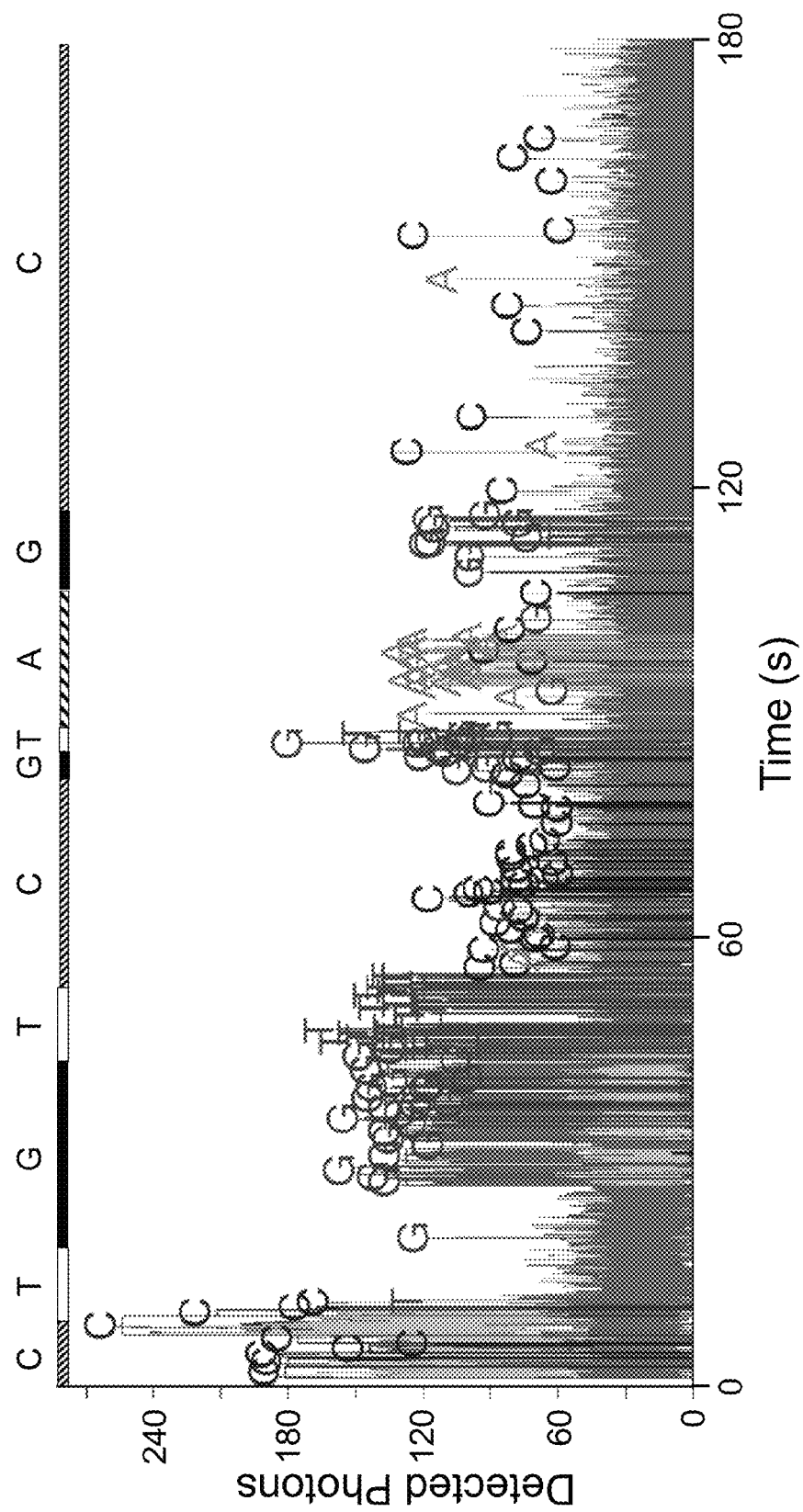

Four-color template-directed sequencing reactions like those described above were performed using as a template a 16S *E. coli* rRNA molecule (1.5 kb), which comprises a pseudouridine residue at position 516. FIG. 6 provides data showing detection of pseudouridine in the rRNA template during template-directed nascent strand synthesis. FIG. 6A provides the structure of pseudouridine, and FIG. 6B illustrates the position of the pseudouridine residue in the 16S rRNA template. FIG. 6C is a plot showing the length of the duration of incorporation is lengthened in the vicinity of the pseudouridine residue. FIG. 6D provides bulk data illustrating that different sets of phospholabeled nucleotides can affect polymerase activity (incorporation duration) on a template molecule. FIGS. 6E and 6F show representative time traces of fluorescence intensity from individual ZMWs. The trace in FIG. 6E is from the portion of the rRNA comprising the pseudouridine residue. The large block of A sampling and incorporating is indicative of the pseudouridine residue. In contrast, the trace in FIG. 6F is from a portion of the rRNA template that does not contain a pseudouridine residue, and there is no large block of A sampling. These results demonstrated that the methods described herein are capable of single-molecule, real-time RNA sequencing, and that the methods can be used to detect pseudouridine bases in an RNA template.

Figure 7A:
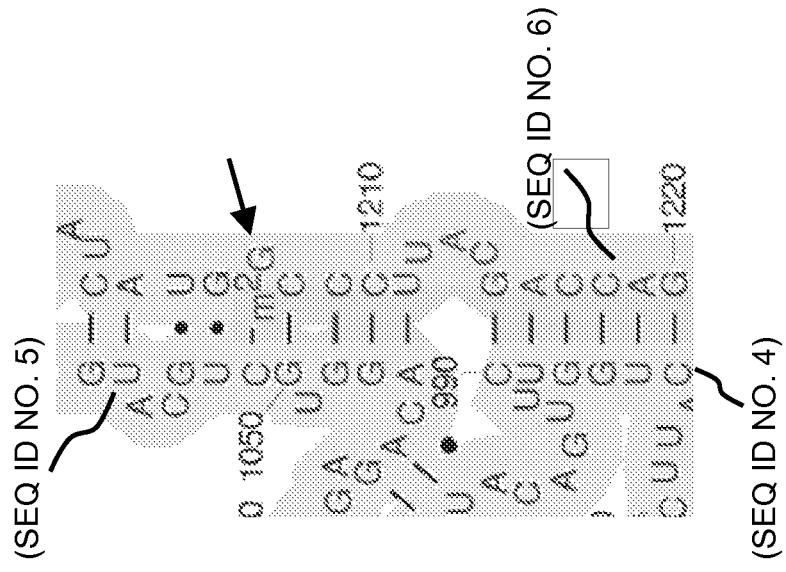
Figure 7B:
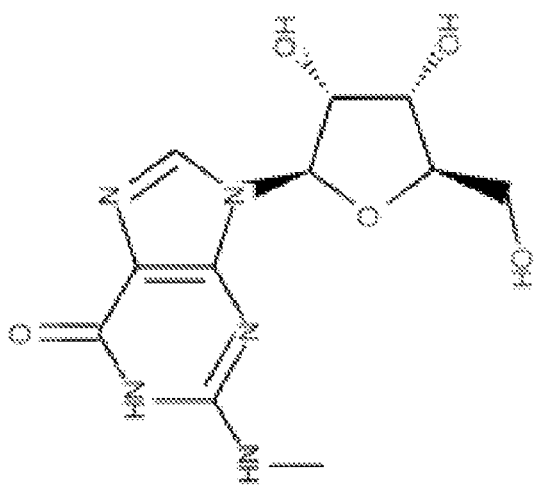

Four-color template-directed sequencing reactions like those described above were performed using as a template a 16S *E. coli* rRNA molecule, which comprising an $N^2$-methylguanosine residue at position 1207. FIG. 7 provides data showing detection of $N^2$-methylguanosine in the rRNA template during template-directed nascent strand synthesis. FIG. 7A provides the structure of $N^2$-methylguanosine, and FIG. 7B illustrates the position of the $N^2$-methylguanosine residue in the 16S rRNA template. FIG. 7C provides bulk data illustrating that the length of the duration of incorporation is lengthened in the vicinity of the $N^2$-methylguanosine residue.

Figure 8:
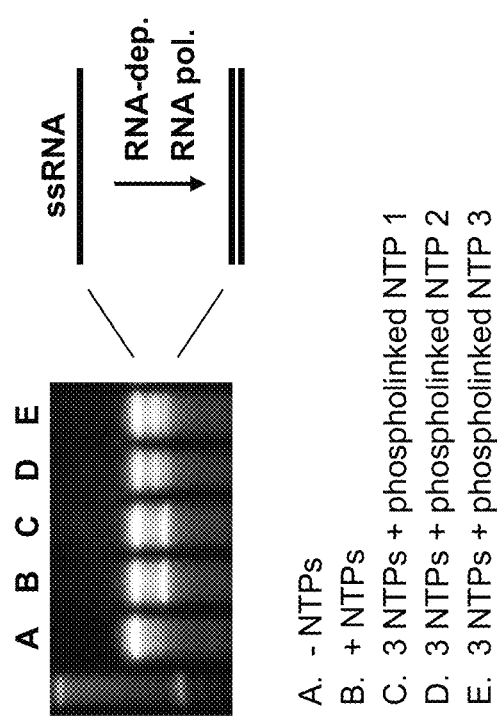
FIG. 8 provides results from template-dependent synthesis reactions using an RNA-dependent RNA polymerase.

Template-directed sequencing reactions like those described above were performed using an RNA template and an RNA-dependent RNA polymerase. The gel illustrated in FIG. 8 has the following lane assignments: A. –NTPs (negative control); B. unmodified dNTPs (positive control); C. a first phospholinked dNTP replacing an unmodified dNTP; D. a second phospholinked dNTP replacing an unmodified dNTPs; E. a third phospholinked dNTP replacing an unmodified dNTP. These results demonstrate not only that template-directed RNA sequencing can be carried out by an RNA-dependent RNA polymerase, but that different phospholinked nucleotide analogs can have different affects on the activity of the polymerase enzyme.

It is to be understood that the above description is intended to be illustrative and not restrictive. It readily should be apparent to one skilled in the art that various embodiments and -modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes.

The invention claimed is:

1. A method for identifying a secondary structure of an RNA molecule, the method comprising:
   (a) providing the RNA molecule, wherein the RNA molecule comprises a secondary structure important to the biological function of the RNA molecule;
   (b) binding a sequencing engine to the RNA molecule to produce a complex;
   (c) immobilizing the complex in an optical confinement such that the optical confinement contains only one such complex;
   (d) introducing a reaction mixture comprising a set of labeled nucleotides to the optical confinement;
   (e) processing the RNA molecule with the sequencing engine, thereby generating a sequence read for the RNA molecule; and
   (f) detecting an energetic profile of the sequencing engine during the processing, wherein the energetic profile is indicative of the secondary structure, thereby identifying the secondary structure in the RNA molecule within the sequence read.

2. The method of claim 1, wherein the reaction mixture is adjusted to modulate the energetic profile of the sequencing engine in response to the secondary structure.

3. The method of claim 2, wherein at least one of the temperature, ionic strength, and pH of the reaction mixture is adjusted.

4. The method of claim 2, wherein an agent known to affect the stability of the secondary structure is added to the reaction mixture.

5. The method of claim 1, wherein the RNA molecule is selected from the group consisting of mRNA, rRNA, tRNA, miRNA, siRNA, piRNA, and long ncRNA.

6. The method of claim 1, wherein the RNA molecule comprises a base modification.

7. The method of claim 1, wherein the sequencing engine is an RNA-dependent RNA polymerase or a reverse transcriptase.

8. The method of claim 7, wherein the sequencing engine is phi6 polymerase.

9. The method of claim 1, wherein the energetic profile comprises a member selected from: a pause in the processing by the sequencing engine, a change in incorporation duration, a change in interpulse duration, and a change in missed or extra pulses.

10. The method of claim 1, wherein the processing comprises performing a sequencing-by-synthesis reaction.

11. The method of claim 10, wherein the processing comprises cognate sampling.

12. The method of claim 11, wherein the set of labeled nucleotides comprises unincorporatable nucleotides, and wherein the introducing further comprises introducing a set of unlabeled incorporatable nucleotides to the optical confinement.

13. The method of claim 1, wherein the sequencing engine is bound, directly or indirectly, to a surface of the optical confinement.

14. The method of claim 1, wherein the RNA molecule is bound, directly or indirectly, to a surface of the optical confinement.

15. The method of claim 14, wherein the RNA molecule is hybridized to an oligonucleotide bound to a surface of the optical confinement.

* * * * *